(12) United States Patent
Essex et al.

(10) Patent No.: US 11,406,275 B2
(45) Date of Patent: Aug. 9, 2022

(54) IMPEDANCE MEASUREMENT SYSTEM

(71) Applicant: Impedimed Limited, Pinkenba (AU)

(72) Inventors: Tim Essex, Wakerley (AU); Matthew Joseph Miller, Carlsbad, CA (US)

( * ) Notice: Subject to any disclaimer, the term of this patent is extended or adjusted under 35 U.S.C. 154(b) by 403 days.

(21) Appl. No.: 15/774,967

(22) PCT Filed: Nov. 8, 2016

(86) PCT No.: PCT/AU2016/051069
§ 371 (c)(1),
(2) Date: May 9, 2018

(87) PCT Pub. No.: WO2017/079793
PCT Pub. Date: May 18, 2017

(65) Prior Publication Data
US 2018/0333071 A1 Nov. 22, 2018

Related U.S. Application Data

(60) Provisional application No. 62/346,941, filed on Jun. 7, 2016.

(30) Foreign Application Priority Data

Nov. 10, 2015 (AU) ................................ 2015904624

(51) Int. Cl.
*A61B 5/053* (2021.01)
*A61B 5/00* (2006.01)
(Continued)

(52) U.S. Cl.
CPC .......... *A61B 5/0537* (2013.01); *A61B 5/0004* (2013.01); *A61B 5/0022* (2013.01);
(Continued)

(58) Field of Classification Search
None
See application file for complete search history.

(56) References Cited

U.S. PATENT DOCUMENTS

D254,504 S * 3/1980 Myers .......................... D24/133
5,337,230 A * 8/1994 Baumgartner ....... A61B 5/0424
700/9

(Continued)

FOREIGN PATENT DOCUMENTS

WO  WO 2001/028416 A1  4/2001

OTHER PUBLICATIONS

International Search Report and Written Opinion dated Dec. 23, 2016 for Application No. PCT/AU2016/051069.

*Primary Examiner* — Benjamin S Melhus
(74) *Attorney, Agent, or Firm* — Knobbe, Martens, Olson & Bear, LLP

(57) ABSTRACT

A system for performing at least one impedance measurement on a biological subject, the system including a measuring device having a signal generator that generates a drive signal, a sensor that measures a response signal and a measuring device processor that at least in part controls the at least one signal generator and receives an indication of a measured response signal from the at least one sensor, allowing the at least one impedance measurement to be performed. The system also includes a connectivity module having a connectivity module housing and electrodes that are provided in electrical contact with the subject in use. Respective first and second connectors are used to electrically connect the sensor and signal generator to the electrodes allowing a drive signal to be applied to the subject via first electrodes and allowing the response signal to be measured via second electrodes so that the at least one impedance measurement can be performed.

22 Claims, 24 Drawing Sheets

(51) Int. Cl.
*A61B 5/0537* (2021.01)
*A61B 5/0245* (2006.01)
*A61B 5/08* (2006.01)

(52) U.S. Cl.
CPC .......... *A61B 5/0245* (2013.01); *A61B 5/0816* (2013.01); *A61B 5/4872* (2013.01); *A61B 5/4875* (2013.01); *A61B 5/4878* (2013.01); *A61B 5/4881* (2013.01); *A61B 5/6825* (2013.01); *A61B 5/6829* (2013.01); *A61B 5/742* (2013.01); *A61B 5/7405* (2013.01); *A61B 5/7445* (2013.01); *A61B 5/6887* (2013.01); *A61B 2560/0228* (2013.01); *A61B 2560/045* (2013.01); *A61B 2560/0456* (2013.01); *A61B 2562/0209* (2013.01); *A61B 2562/04* (2013.01); *A61B 2562/222* (2013.01); *A61B 2562/227* (2013.01)

(56) References Cited

U.S. PATENT DOCUMENTS

| | | | | |
|---|---|---|---|---|
| 5,415,176 | A * | 5/1995 | Sato | A61B 5/0537 177/245 |
| 5,579,782 | A * | 12/1996 | Masuo | A61B 5/0537 600/382 |
| 5,817,031 | A * | 10/1998 | Masuo | A61B 5/0537 600/547 |
| 6,243,651 | B1 * | 6/2001 | Masuo | A61B 5/0537 600/547 |
| 6,256,532 | B1 * | 7/2001 | Cha | A61B 5/0537 177/245 |
| 6,400,983 | B1 * | 6/2002 | Cha | A61B 5/0537 600/547 |
| 6,490,481 | B1 * | 12/2002 | Komatsu | A61B 5/4872 600/372 |
| 6,551,257 | B1 * | 4/2003 | Sunako | A61B 5/0537 600/587 |
| D479,332 | S * | 9/2003 | Leventhal | D24/186 |
| 6,714,814 | B2 * | 3/2004 | Yamada | A61B 5/0537 600/384 |
| 6,790,178 | B1 * | 9/2004 | Mault | A61B 5/02055 600/300 |
| D503,119 | S * | 3/2005 | Motomizu | D10/92 |
| D524,944 | S * | 7/2006 | Collins | D24/186 |
| 7,262,703 | B2 * | 8/2007 | Collins | A61B 5/0537 340/539.12 |
| D578,917 | S * | 10/2008 | Otsuka | D10/94 |
| D580,806 | S * | 11/2008 | Otsuka | D10/94 |
| D582,813 | S * | 12/2008 | Otsuka | D10/94 |
| D609,706 | S * | 2/2010 | Helt, III | D14/426 |
| 8,290,580 | B2 * | 10/2012 | Horiguchi | A61N 1/326 607/2 |
| 8,548,556 | B2 * | 10/2013 | Jensen | A61B 5/0537 600/384 |
| 8,892,198 | B2 * | 11/2014 | Bohorquez | A61B 5/0537 600/547 |
| 8,934,226 | B2 * | 1/2015 | Smith | G06F 1/1613 361/679.2 |
| 9,113,808 | B2 * | 8/2015 | Bohorquez | A61B 5/053 |
| 9,861,293 | B2 * | 1/2018 | Lupton | A61B 5/6843 |
| D811,914 | S * | 3/2018 | Essex | D10/94 |
| D811,915 | S * | 3/2018 | Essex | D10/94 |
| 10,653,334 | B2 * | 5/2020 | Cosentino | A61B 5/0004 |
| 2004/0199057 | A1 * | 10/2004 | Hasegawa | A61B 5/7475 600/300 |
| 2004/0220492 | A1 * | 11/2004 | Kodama | G01G 19/50 600/547 |
| 2005/0059902 | A1 * | 3/2005 | Itagaki | A61B 5/0537 600/547 |
| 2005/0070778 | A1 * | 3/2005 | Lackey | A61B 5/4875 600/366 |
| 2005/0171451 | A1 * | 8/2005 | Yeo | A61B 5/0002 600/547 |
| 2005/0187486 | A1 * | 8/2005 | Shimomura | A61B 5/0537 600/547 |
| 2005/0215918 | A1 * | 9/2005 | Frantz | A61B 5/6831 600/547 |
| 2006/0206271 | A1 * | 9/2006 | Oshima | A61B 5/4872 702/19 |
| 2006/0282005 | A1 * | 12/2006 | Kasahara | A61B 5/0537 600/547 |
| 2007/0038140 | A1 * | 2/2007 | Masuo | A61B 5/0537 600/547 |
| 2007/0208241 | A1 * | 9/2007 | Drucker | A61B 5/4872 600/323 |
| 2008/0039700 | A1 * | 2/2008 | Drinan | A61B 5/6804 600/301 |
| 2008/0146961 | A1 * | 6/2008 | Okura | A61B 5/107 600/547 |
| 2008/0287823 | A1 * | 11/2008 | Chetham | A61B 5/0537 600/547 |
| 2009/0018464 | A1 * | 1/2009 | Watanabe | A61B 5/0537 600/547 |
| 2009/0089672 | A1 * | 4/2009 | Tseng | A61B 5/0537 715/700 |
| 2009/0143663 | A1 * | 6/2009 | Chetham | A61B 5/053 600/372 |
| 2009/0182243 | A1 * | 7/2009 | Oku | A61B 5/4872 600/547 |
| 2009/0264790 | A1 * | 10/2009 | Ashida | A61B 5/0537 600/547 |
| 2010/0100003 | A1 * | 4/2010 | Chetham | A61B 5/6829 600/547 |
| 2010/0168530 | A1 * | 7/2010 | Chetham | A61B 5/0537 600/301 |
| 2011/0087129 | A1 * | 4/2011 | Chetham | A61B 5/7203 600/547 |
| 2011/0196617 | A1 | 8/2011 | Petrucelli | |
| 2011/0213268 | A1 * | 9/2011 | Kosaka | G01G 21/28 600/547 |
| 2011/0237926 | A1 * | 9/2011 | Jensen | A61B 5/0537 600/393 |
| 2012/0108917 | A1 * | 5/2012 | Libbus | A61B 5/0006 600/301 |
| 2013/0023747 | A1 * | 1/2013 | Karo | A61B 5/4872 600/384 |
| 2014/0378860 | A1 * | 12/2014 | Nakamura | A61B 5/1118 600/547 |
| 2015/0296963 | A1 * | 10/2015 | Byun | G04G 17/08 224/191 |
| 2015/0351690 | A1 * | 12/2015 | Toth | A61B 5/6833 600/373 |
| 2016/0015276 | A1 * | 1/2016 | Strauss | A61B 5/0205 600/301 |
| 2017/0209318 | A1 * | 7/2017 | Schroeder | B64C 1/20 |

* cited by examiner

IMPEDANCE MEASUREMENT SYSTEM

RELATED APPLICATIONS

This application is a U.S. National Phase under 35 U.S.C. § 371 of the International Patent Application No. PCT/AU2016/051069, filed Nov. 8, 2016, and published in English on May 18, 2017 as WO/2017/079793, which claims the benefit of Australian Patent Application No. 2015904624, filed Nov. 10, 2015 and U.S. Provisional Application No. 62/346,941, each of which is incorporated by reference in its entirety.

BACKGROUND OF THE INVENTION

The present invention relates to a system and method for performing at least one impedance measurement on a biological subject.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

WO2007/002991 describes apparatus for performing impedance measurements on a subject. The apparatus includes a first processing system for determining an impedance measurement procedure and determining instructions corresponding to the measurement procedure. A second processing system is provided for receiving the instructions, using the instructions to generate control signals, with the control signals being used to apply one or more signals to the subject. The second processing system then receives first data indicative of the one or more signals applied to the subject, second data indicative of one or more signals measured across the subject and performs at least preliminary processing of the first and second data to thereby allow impedance values to be determined.

SUMMARY OF THE PRESENT INVENTION

In one broad form the present invention seeks to provide a system for performing at least one impedance measurement on a biological subject, the system including:
a) a measuring device including:
  i) at least one signal generator that generates a drive signal;
  ii) at least one sensor that measures a response signal;
  iii) a measuring device processor that at least in part controls the at least one signal generator and receives an indication of a measured response signal from the at least one sensor, allowing the at least one impedance measurement to be performed; and,
  iv) a first connector electrically connected to the at least one sensor and the at least one signal generator; and,
b) a connectivity module including:
  i) a connectivity module housing;
  ii) electrodes that are provided in electrical contact with the subject in use; and,
  iii) a second connector electrically connected to the electrodes, wherein in use the measuring device is connected to the connectivity module by interconnecting the first and second connectors so that first electrodes are electrically connected to the at least one signal generator and a second electrodes are electrically connected to the at least one sensor, thereby allowing a drive signal to be applied to the subject via the first electrodes and allowing the response signal to be measured via the second electrodes so that the at least one impedance measurement can be performed.

In one broad form the present invention seeks to provide a method of performing at least one impedance measurement on a biological subject using a system including:
a) a measuring device including:
  i) a measuring device housing;
  ii) at least one signal generator that generates a drive signal;
  iii) at least one sensor that measures a response signal;
  iv) a measuring device processor that at least in part controls the at least one signal generator and receives an indication of a measured response signal from the at least one sensor, allowing the at least one impedance measurement to be performed; and,
  v) a first connector electrically connected to the at least one sensor and the at least one signal generator; and,
b) a connectivity module including:
  i) a connectivity module housing;
  ii) electrodes that are provided in electrical contact with the subject in use; and,
  iii) a second connector electrically connected to the electrodes, wherein in use the measuring device is connected to the connectivity module by interconnecting the first and second connectors so that a first electrodes are electrically connected to the at least one signal generator and a second electrodes are electrically connected to the at least one sensor, thereby allowing a drive signal to be applied to the subject via the first electrodes and allowing the response signal to be measured via the second electrodes so that the at least one impedance measurement can be performed, wherein the method includes:
    (1) determining at least one performable impedance measurement based on a connectivity module type of the connected connectivity module;
    (2) controlling the at least one signal generator and the at least one sensor to generate a drive signal and measure the resulting response signal;
    (3) determining an indication of the drive signal and measured response signal; and,
    (4) determining at least one impedance value indicative of a measured impedance.

In one broad form the present invention seeks to provide a method of performing at least one impedance measurement on a biological subject using a system including:
a) a measuring device including:
  i) a measuring device housing;
  ii) at least one signal generator that generates a drive signal;
  iii) at least one sensor that measures a response signal;
  iv) a measuring device processor that at least in part controls the at least one signal generator and receives an indication of a measured response signal from the at least one sensor, allowing the at least one impedance measurement to be performed; and,
  v) a first connector electrically connected to the at least one sensor and the at least one signal generator; and,
b) a connectivity module including:
  i) a connectivity module housing;

ii) electrodes that are provided in electrical contact with the subject in use; and,
iii) a second connector electrically connected to the electrodes, wherein in use the measuring device is connected to the connectivity module by interconnecting the first and second connectors so that a first electrodes are electrically connected to the at least one signal generator and a second electrodes are electrically connected to the at least one sensor, thereby allowing a drive signal to be applied to the subject via the first electrodes and allowing the response signal to be measured via the second electrodes so that the at least one impedance measurement can be performed; and,
c) a processing system, wherein the method includes:
i) determining at least one performable impedance measurement based on a connectivity module type of a connectivity module connected to the measuring device;
ii) displaying an indication of the at least one performable impedance measurement to a user;
iii) determining a selected performable impedance measurement in accordance with user input commands;
iv) causing the measuring device to perform the selected performable impedance measurement; and,
v) determining at least one impedance value indicative of a measured impedance.

In one broad form the present invention seeks to provide a system for performing at least one impedance measurement on a biological subject, the system including:
a) a measuring device including:
i) at least one signal generator that generates a drive signal;
ii) at least one sensor that measures a response signal;
iii) a measuring device processor that at least in part controls the at least one signal generator and receives an indication of a measured response signal from the at least one sensor, allowing the at least one impedance measurement to be performed; and,
iv) a first connector electrically connected to the at least one sensor and the at least one signal generator; and,
b) a connectivity module including:
i) a connectivity module housing;
ii) electrodes that are provided in electrical contact with the subject in use; and,
iii) a second connector electrically connected to the electrodes, wherein in use the measuring device is connected to the connectivity module by interconnecting the first and second connectors so that first electrodes are electrically connected to the at least one signal generator and a second electrodes are electrically connected to the at least one sensor, thereby allowing a drive signal to be applied to the subject via the first electrodes and allowing the response signal to be measured via the second electrodes so that the at least one impedance measurement can be performed.

In one broad form the present invention seeks to provide a method of performing at least one impedance measurement on a biological subject using a system including:
a) a measuring device including:
i) at least one signal generator that generates a drive signal;
ii) at least one sensor that measures a response signal;
iii) a measuring device processor that at least in part controls the at least one signal generator and receives an indication of a measured response signal from the at least one sensor, allowing the at least one impedance measurement to be performed; and,
iv) a first connector electrically connected to the at least one sensor and the at least one signal generator; and,
b) a connectivity module including:
i) a connectivity module housing;
ii) electrodes that are provided in electrical contact with the subject in use; and,
iii) a second connector electrically connected to the electrodes, wherein in use the measuring device is connected to the connectivity module by interconnecting the first and second connectors so that a first electrodes are electrically connected to the at least one signal generator and a second electrodes are electrically connected to the at least one sensor, thereby allowing a drive signal to be applied to the subject via the first electrodes and allowing the response signal to be measured via the second electrodes so that the at least one impedance measurement can be performed, wherein the method includes:
(1) determining at least one performable impedance measurement based on a connectivity module type of the connected connectivity module;
(2) controlling the at least one signal generator and the at least one sensor to generate a drive signal and measure the resulting response signal;
(3) determining an indication of the drive signal and measured response signal; and,
(4) determining at least one impedance value indicative of a measured impedance.

In one broad form the present invention seeks to provide a method of performing at least one impedance measurement on a biological subject using a system including:
a) a measuring device including:
i) at least one signal generator that generates a drive signal;
ii) at least one sensor that measures a response signal;
iii) a measuring device processor that at least in part controls the at least one signal generator and receives an indication of a measured response signal from the at least one sensor, allowing the at least one impedance measurement to be performed; and,
iv) a first connector electrically connected to the at least one sensor and the at least one signal generator; and,
b) a connectivity module including:
i) a connectivity module housing;
ii) electrodes that are provided in electrical contact with the subject in use; and,
iii) a second connector electrically connected to the electrodes, wherein in use the measuring device is connected to the connectivity module by interconnecting the first and second connectors so that a first electrodes are electrically connected to the at least one signal generator and a second electrodes are electrically connected to the at least one sensor, thereby allowing a drive signal to be applied to the subject via the first electrodes and allowing the response signal to be measured via the second electrodes so that the at least one impedance measurement can be performed; and,
c) a processing system, wherein the method includes:
i) determining at least one performable impedance measurement based on a connectivity module type of a connectivity module connected to the measuring device;

ii) displaying an indication of the at least one performable impedance measurement to a user;
iii) determining a selected performable impedance measurement in accordance with user input commands;
iv) causing the measuring device to perform the selected performable impedance measurement; and,
v) determining at least one impedance value indicative of a measured impedance.

Typically the measuring device is adapted to be used with a number of different connectivity module types, and wherein the measuring device processor performs the at least one impedance measurement at least in part depending on the connectivity module type of a connected connectivity module.

Typically the measuring device processor:
a) determines a connectivity module type of the connected connectivity module; and,
b) in accordance with the determined connectivity module type, at least one of:
  i) causes the at least one impedance measurement to be performed; and,
  ii) processes a measured response signal to determine at least one impedance value indicative of a measured impedance.

Typically the connectivity module type is determined using at least one of:
a) a configuration of connections between the first and second connectors;
b) a configuration of the second connector; and,
c) a property of an electrical component electrically connected to the second connector.

Typically the first and second connectors include a plurality of individual connections, and wherein the connectivity module type is determined based at least in part on connections between individual connections of the second connector.

Typically the measuring device includes at least one contact switch, and wherein the switch is selectively actuated by the connectivity module housing when the measuring device and connectivity module are connected.

Typically the measuring device processor:
a) determines an identifier associated with the connectivity module; and,
b) determines the connectivity module type using the identifier.

Typically the connectivity module includes a memory and wherein the measuring device processor retrieves the identifier from the memory via at least one of:
a) a wireless connection; and,
b) the first and second connectors.

Typically the connectivity module includes a memory and wherein the measuring device processor:
a) retrieves instructions from the memory via at least one of:
  i) a wireless connection; and,
  ii) the first and second connectors; and,
b) causes at least one impedance measurement to be performed in accordance with the instructions.

Typically the measuring device processor determines at least one impedance value indicative of at least one measured impedance using:
a) an indication of at least one drive signal applied to the subject;
b) an indication of at least one measured response signal; and,
c) calibration data stored in a memory.

Typically the calibration data includes:
a) first calibration data specific to the measuring device; and,
b) second calibration data specific to the connectivity module.

Typically the measuring device processor determines the calibration data at least in part using at least one of:
a) a connectivity module type; and,
b) a connectivity module identifier.

Typically the measuring device processor selects one of a number of calibration data sets stored in a memory.

Typically the first and second connectors include a multi-pin plug and a corresponding multi-pin socket.

Typically the measuring device housing and connectivity module housing are configured to physically interconnect when the measuring device is connected to the connectivity module.

Typically the electrodes are mounted on the connectivity module housing.

Typically the electrodes are coupled to leads extending from the connectivity module housing.

Typically the electrodes form part of at least one electrode sheet.

Typically the at least one electrode sheet includes a substrate and conductive material defining each electrode, the conductive material being at least one of:
a) impregnated in the substrate; and,
b) printed on a surface of the substrate.

Typically the electrode sheet includes a lead connector electrically coupled to the electrodes and that is coupled to at least one lead in use.

Typically the lead connector includes a flexible tab extending from the substrate.

Typically the connectivity module includes at least one buffer circuit coupled to each electrode.

Typically the measuring device includes a switching unit for selectively electrically connecting the at least one signal generator and the at least one sensor to the first connector thereby allowing the at least one signal generator and the at least one sensor to be selectively connected to different electrodes.

Typically the measuring device processor controls the switching unit to thereby selectively electrically connect the at least one signal generator and the at least one sensor to respective electrodes thereby allowing a respective impedance measurement to be performed.

Typically the measuring device includes:
a) four signal generators, each being electrically connected to a respective drive electrode; and,
b) four sensors, each being electrically connected to a respective sense electrode and wherein the measuring device processor selectively activates the at least one signal generators and sensors to thereby allow a respective impedance measurement to be performed.

Typically the measuring device includes an input button that at least one of:
a) activates the measuring device; and,
b) causes at least one impedance measurement to be performed.

Typically the measuring device includes an indicator, and wherein the measuring device processor uses the indicator to indicate at least one of:
a) completion of an impedance measurement;
b) performing of an impedance measurement;
c) connection of the measuring device to at least one of:
  i) a connectivity module; and,
  ii) a processing system.

Typically the indicator includes at least one of:
a) an optical indicator;
b) a multi-colour LED; and,
c) a speaker.

Typically the measuring device includes an interface that allows the measuring device processor to communicate with a processing system using at least one of wired and wireless communications.

Typically the system includes a processing system that:
a) determines at least one impedance measurement to be performed;
b) causes the measuring device to perform the at least one impedance measurement; and,
c) receives an indication of at least one impedance value from the measuring device, the at least one impedance value being indicative of a measured impedance.

Typically the measuring device processor communicates with the processing system to at least one of:
a) determine the at least one impedance measurement to be performed; and,
b) provide the indication of at least one impedance value to the processing system.

Typically the processing system:
a) determines an impedance measurement process to be performed, the impedance measurement process including a sequence of impedance measurements; and,
b) causes the measuring device processor to perform the sequence of impedance measurements.

Typically the processing system processes the at least one impedance measurement to determine at least one indicator indicative of a biological state of the subject.

Typically the processing system displays a user interface allowing a user to at least one of:
a) select at least one impedance measurement to be performed;
b) select an impedance measurement process to be performed, the impedance measurement process including a sequence of impedance measurements;
c) view at least one impedance measurement; and,
d) view at least one indicator indicative of a biological state of the subject.

Typically:
a) the measuring device processor:
  i) determines at least one performable impedance measurement based on a connectivity module type of a connected connectivity module;
  ii) provides an indication of the at least one performable impedance measurement to the processing system; and,
b) the processing system:
  i) displays an indication of the at least one performable impedance measurement to a user;
  ii) determines a selected performable impedance measurement in accordance with user input commands; and,
  iii) causes the measuring device to perform the selected performable impedance measurement.

Typically the system includes a processing system that:
a) determines at least one performable impedance measurement based on a connectivity module type of a connectivity module connected to the measuring device;
b) displays an indication of the at least one performable impedance measurement to a user;
c) determines a selected performable impedance measurement in accordance with user input commands;
d) causes the measuring device to perform the selected performable impedance measurement; and,
e) determines at least one impedance value indicative of a measured impedance.

Typically the measuring device is provided within the connectivity module housing.

Typically the measuring device includes a circuit board having the at least one signal generator, the at least one sensor and first connector mounted thereon.

Typically the circuit board is supported internally within the connectivity module using at least one of:
a) physical engagement between the first and second connectors; and,
b) a mounting within the connectivity module housing.

Typically the connectivity module includes first and second housings.

Typically the first housing includes spaced pairs of foot drive and sense electrodes and the second housing including spaced pairs of hand drive and sense electrodes.

Typically the drive and sense electrodes are spaced apart metal plates.

Typically the first housing includes a raised lip extending at least partially around each pair of foot drive and sense electrodes to thereby guide positioning of a subject's foot relative to the foot drive and sense electrodes in use.

Typically the raised lip is configured to engage at least a heel of the user.

Typically the second housing is shaped to at least partially conform to a shape of a user's hands.

Typically the second housing includes a raised portion between each pair of hand drive and sense electrodes, the raised portion defining thumb recesses to thereby guide positioning of a subject's hands relative to each pair of hand drive and sense electrodes in use.

Typically the second housing includes a processing system mounting that in use receives a support containing a processing system.

Typically the second housing includes a processing system mounting that in use receives a support containing a processing system.

Typically at least one of the first and second housings include keyhole mountings, allowing the at least one of the first and second housings to be removably mounted to a pedestal.

It will be appreciated that the broad forms of the invention can be used in conjunction and/or independently, and reference to separate broad forms in not intended to be limiting.

BRIEF DESCRIPTION OF THE DRAWINGS

An example of the present invention will now be described with reference to the accompanying drawings, in which:—

DETAILED DESCRIPTION OF THE PREFERRED EMBODIMENTS

Figure 1:
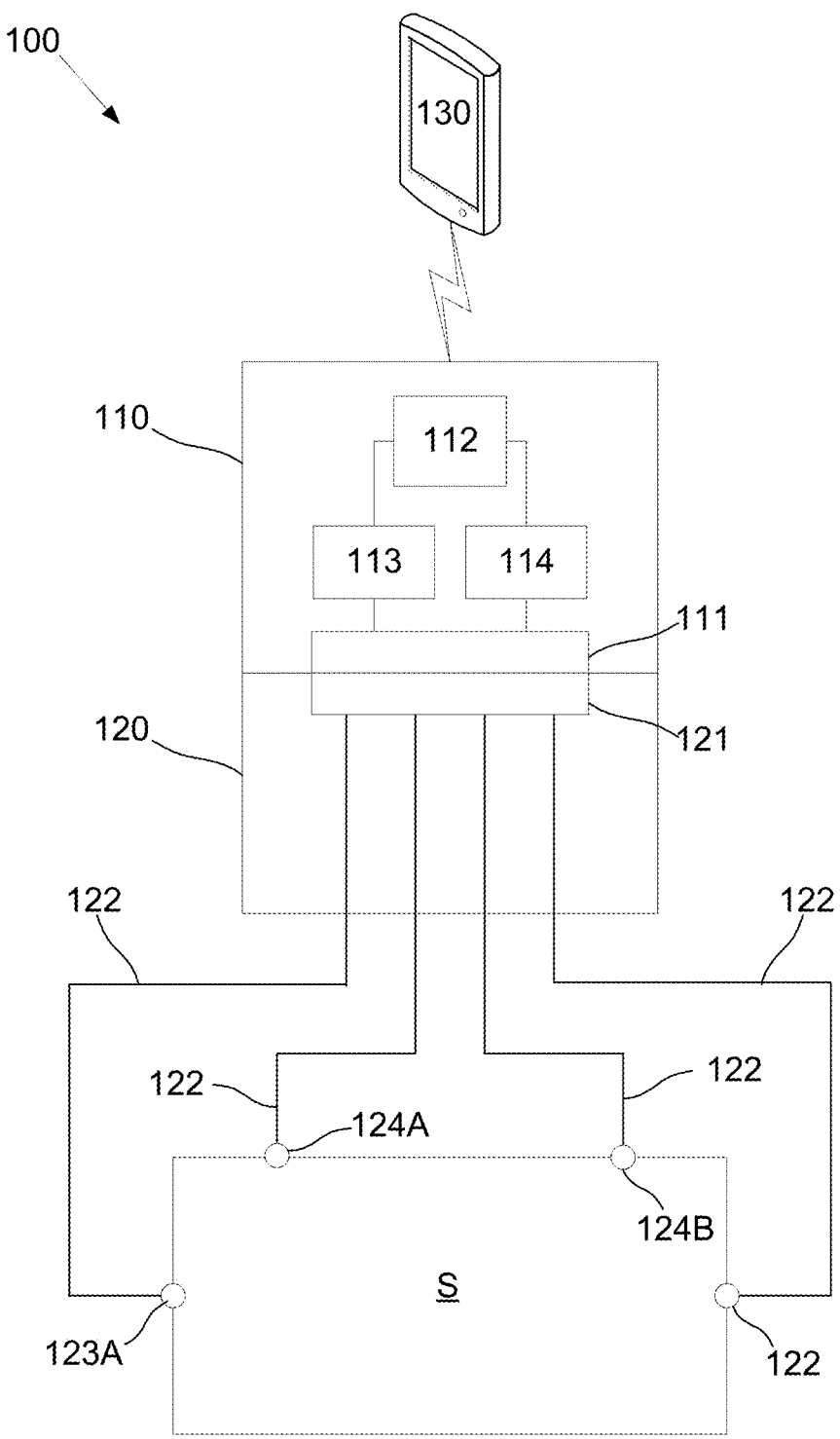
FIG. 1 is a schematic diagram of an example of a system for performing at least one impedance measurement on a biological subject.

An example of apparatus suitable for performing at least one impedance measurement on a biological subject will now be described with reference to FIG. 1.

As shown the system 100 includes a measuring device 110 coupled to a connectivity module 120. An optional client device, such as a computer system, smartphone, tablet or the like, can also be provided in communication with the measuring device, allowing operation of the measuring device to be at least partially controlled, although this is not essential and will depend on the preferred implementation.

The measuring device 110 includes a measuring device housing containing at least one signal generator 113 that generates a drive signal and at least one sensor 114 that measures a response signal. A measuring device processor 112 is provided that at least in part controls the signal generator 113 and receives an indication of a measured response signal from the sensor 114 allowing the at least one impedance measurement to be performed. The measuring device 110 further includes a first connector 111 electrically connected to at least the at least one sensor 114 and the at least one signal generator 113.

The connectivity module 120 includes a connectivity module housing, and a number of electrodes 123, 124, that are provided in electrical contact with the subject S in use. The electrodes can be attached to or form part of the housing, or could be connected to the housing via respective leads 122, and example arrangements will be described in more detail below. The connectivity module also includes a second connector 121 electrically connected to the electrodes 123, 124.

In use the measuring device 110 is connected to the connectivity module 120 by interconnecting the first and second connectors 111, 121 so first electrodes 123 are electrically connected to the at least one signal generator and second electrodes 124 are electrically connected to the at least one sensor, thereby allowing a drive signal to be applied to the subject via the first electrodes 123 (referred to generally as drive electrodes) and allowing the response signal to be measured via the second electrodes 124 (referred to generally as sense electrodes) so that the at least one impedance measurement can be performed.

In the above described arrangement, a separate measuring device 110 and connectivity module 120 are used, allowing a single type of measuring device 110 to be configured for use with multiple different types of connectivity module 120. This in turn enables a range of different impedance measurements to be performed using different configurations of connectivity module. In this regard, different electrode arrangements 123, 124 may be required for performing different types of impedance measurement, and so the provision of a common measuring device, and different types of connectivity module allows a single measuring device to be used in a wider range of circumstances than would be possible for a single integrated device.

For example, the connectivity module 120 could include stand-on plates and hand grip electrodes for use in measuring aspects of a subject's body composition, whilst adhesive electrodes positioned on the wrist and ankles might be preferred for oedema detection, or the like. In this instance, by allowing a common measuring device to be selectively connected to different connectivity modules, this allows the most suitable electrode configuration to be used, whilst allowing a common measuring device design to be used, which can reduce overall hardware requirements and allow for greater efficiencies in manufacture.

Furthermore, in one example, the measuring device 110 can be adapted to sense the type of connectivity module 120 to which it is connected, thereby at least partially controlling the impedance measurement process based on the connectivity module currently being used.

Figure 2:
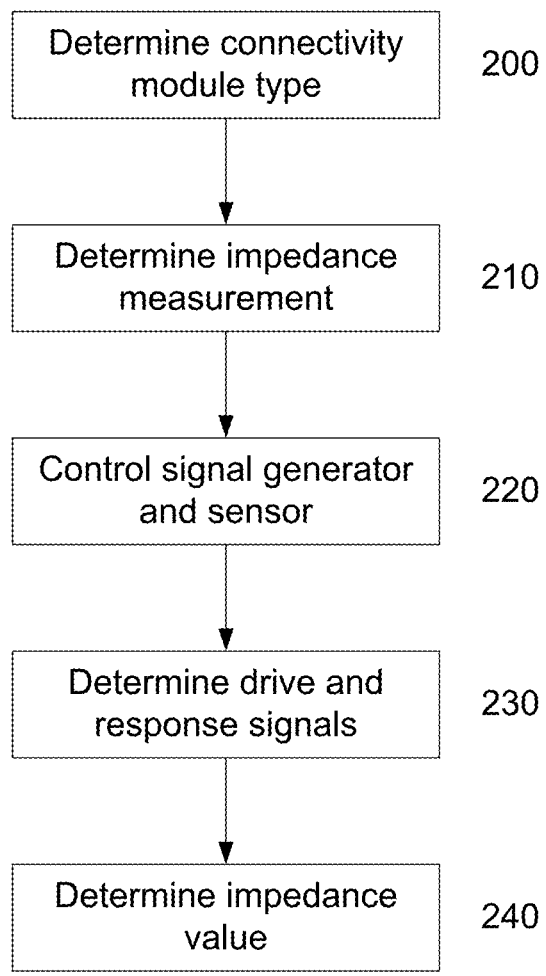
FIG. 2 is a flowchart of an example of a method for performing at least one impedance measurement on a biological subject.

An example of this, will now be described with reference to FIG. 2.

In this example, at step 200, the measuring device processor 112 determines a connectivity module type. This can be achieved in any suitable manner, depending on the preferred implementation and could be based on a configuration of connections between the connectors 111, 121, electrical characteristics or properties of components within the connectivity module, stored identifiers, or the like.

At step 210, the connectivity module type is used to determine the impedance measurements that can be performed using the respective connectivity module 120. This can be performed by the measuring device processor 112, or alternatively could be performed by the client device 130. In any event, different connectivity module types could be associated with respective types of impedance measurement, for example based on the configuration of electrodes and/or any other components provided therein, such as voltage/current buffers or the like. Thus, information regarding the connectivity module type can be used to determine the impedance measurements that can be performed, allowing operation of the system to be controlled accordingly.

Prior to a measurement being performed, the first and second electrodes 123, 124 are positioned on the subject to allow one or more signals to be injected into the subject S, and allowing a response signal to be measured. The location of the electrodes 123, 124 will depend on the segment of the subject S under study. Thus, for example, the electrodes 123, 124 can be placed on the thoracic and neck region of the subject S to allow the impedance of the chest cavity to be determined. Alternatively, positioning electrodes on the wrist and ankles of a subject allows the impedance of limbs, torso and/or the entire body to be determined.

Once positioned, at step 220, the measuring device processor 112 controls the at least one signal generator 113 and the at least one sensor 114, allowing the impedance measurements to be performed. Accordingly, it will be appreciated that the measuring device processor 112 may be any form of electronic processing device capable of performing appropriate control, and could include an FPGA (field programmable gate array), or a combination of a programmed computer system and specialised hardware, or the like.

In particular, the measuring device processor 112 is adapted to generate control signals, which cause the signal generator 113 to generate one or more alternating signals, such as voltage or current signals of an appropriate waveform, which can be applied to a subject S, via the first electrodes 123. The signal generator 113 could therefore be of any appropriate form, but will typically include digital to analogue converters (DACs) for converting digital signals from the processing device to analogue signals, which are amplified to generate the required drive signals.

The nature of the alternating signal will vary depending on the nature of the measuring device and the subsequent analysis being performed. For example, the system can use Bioimpedance Analysis (BIA) in which a single low frequency signal is injected into the subject S, with the measured impedance being used directly in the determination of biological parameters. In one example, the applied signal has a relatively low frequency, such as below 100 kHz, more typically below 50 kHz and more preferably below 10 kHz. In this instance, such low frequency signals can be used as an estimate of the impedance at zero applied frequency, commonly referred to as the impedance parameter value $R_0$, which is in turn indicative of extracellular fluid levels.

Alternatively, the applied signal can have a relatively high frequency, such as above 200 kHz, and more typically above 500 kHz, or 1000 kHz. In this instance, such high frequency signals can be used as an estimate of the impedance at infinite applied frequency, commonly referred to as the impedance parameter value $R_\infty$, which is in turn indicative of a combination of the extracellular and intracellular fluid levels, as will be described in more detail below.

Alternatively and/or additionally, the system can use Bioimpedance Spectroscopy (BIS) in which impedance measurements are performed at each of a number of frequencies ranging from very low frequencies (1 kHz and more typically 3 kHz) to higher frequencies (1000 kHz), and can use as many as 256 or more different frequencies within this range. Such measurements can be performed by applying a signal which is a superposition of plurality of frequencies simultaneously, or a number of alternating signals at different frequencies sequentially, depending on the preferred implementation. The frequency or frequency range of the applied signals may also depend on the analysis being performed.

When impedance measurements are made at multiple frequencies, these can be used to derive one or more impedance parameter values, such as values of $R_0$, $Z_c$, $R_\infty$, which correspond to the impedance at zero, characteristic and infinite frequencies. These can in turn be used to determine information regarding both intracellular and extracellular fluid levels, as will be described in more detail below.

A further alternative is for the system to use Multiple Frequency Bioimpedance Analysis (MFBIA) in which multiple signals, each having a respective frequency are injected into the subject S, with the measured impedances being used in the assessment of fluid levels. In one example, four frequencies can be used, with the resulting impedance measurements at each frequency being used to derive impedance parameter values, for example by fitting the measured impedance values to a Cole model, as will be described in more detail below. Alternatively, the impedance measurements at each frequency may be used individually or in combination.

Thus, the measuring device 110 may either apply an alternating signal at a single frequency, at a plurality of frequencies simultaneously, or a number of alternating signals at different frequencies sequentially, depending on the preferred implementation. The frequency or frequency range of the applied signals may also depend on the analysis being performed.

In one example, the applied signal is generated by a voltage generator, which applies an alternating voltage to the subject S, although alternatively current signals may be applied. In one example, the voltage source is typically symmetrically arranged, with two signal generators 113 being independently controllable, to allow the signal voltage across the subject to be varied, for example to minimise a common mode signal and hence substantially eliminate any imbalance as described in copending patent application number WO2009059351.

As the drive signals are applied to the subject, the sensor 114 then determines the response signal in the form of the voltage across or current through the subject S, using the second electrodes 124. The sensor 114 may include one or more amplifiers for amplifying sensed response signals and analogue to digital converters (ADCs) to digitise the analogue response signals and providing digitised response signals to the processing device.

At step 230, the measuring device processor 112 determines an indication of the applied drive signal and measured response signals. Thus, a voltage difference and/or current is measured between the second electrodes 124. In one example, the voltage is measured differentially, meaning that two sensors 114 are used, with each sensor 114 being used to measure the voltage at each second electrode 124 and therefore need only measure half of the voltage as compared to a single ended system.

Thus, in the above arrangement, four electrodes are shown, with two forming drive electrodes and two forming sense electrodes. However, this is not essential, and any suitable number of electrodes could be used. Furthermore, a single signal generator and sensor are shown, but again a respective signal generator and sensor could be used for each drive and sense electrode, respectively, and the described arrangement is for the purpose of illustration only.

At step 240, the drive and response signals are used to determine an impedance. In this regard, the response signal will be a superposition of voltages generated by the human body, such as the ECG (electrocardiogram), voltages generated by the applied signal, and other signals caused by environmental electromagnetic interference. Accordingly, filtering or other suitable analysis may be employed to remove unwanted components.

The acquired signal is typically demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a signal processing technique such as multiplying the measured signal with a reference sine wave and cosine wave derived from the signal generator, or with measured sine and cosine waves, and integrating over a whole number of cycles. This process, known variously as quadrature demodulation or synchronous detection, rejects all uncorrelated or asynchronous signals and significantly reduces random noise.

Other suitable digital and analogue demodulation techniques will be known to persons skilled in the field.

In the case of BIS, impedance or admittance measurements are determined from the signals at each frequency by comparing the recorded voltage and the current through the subject. The demodulation algorithm can then produce amplitude and phase signals at each frequency, allowing an impedance value at each frequency to be determined.

Whilst the measured impedance can be used directly, in one example, the measured impedance is used to derive an impedance parameter, and in particular an impedance (resistance) at zero frequency, $R_0$, equals the extracellular resistance $R_e$.

Figure 3A:
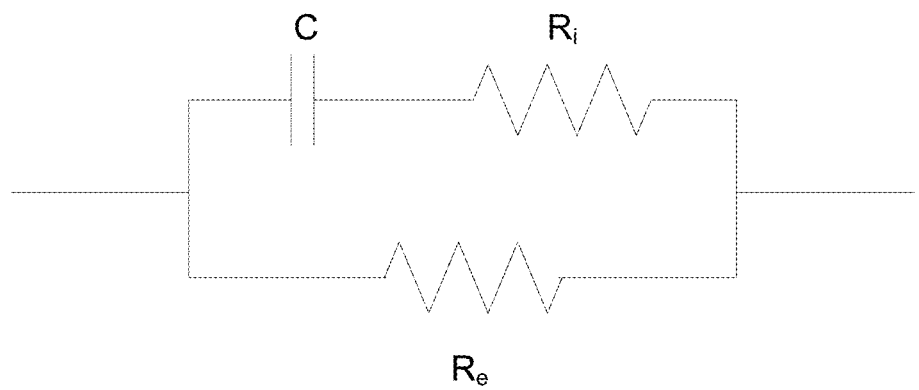
FIG. 3A is a schematic diagram of an example of a theoretical equivalent circuit for biological tissue.

In this regard, FIG. 3A is an example of an equivalent circuit that effectively models the electrical behaviour of biological tissue. The equivalent circuit has two branches that represent current flow through extracellular fluid and intracellular fluid, respectively. The extracellular fluid component of biological impedance is represented by an extracellular resistance $R_e$, whilst the intracellular fluid component is represented by an intracellular resistance $R_i$ and a capacitance C representative of the cell membranes.

The relative magnitudes of the extracellular and intracellular components of impedance of an alternating current (AC) are frequency dependent. At zero frequency the capacitor acts as a perfect insulator and all current flows through the extracellular fluid, hence the resistance at zero frequency, $R_0$, equals the extracellular resistance $R_e$. At infinite frequency the capacitor acts as a perfect conductor and the current passes through the parallel resistive combination. The resistance at infinite frequency $R_\infty$ is given by:

$$R_\infty = \frac{R_e R_i}{R_e + R_i} \quad (1)$$

Hence the intracellular resistance is given by:

$$R_i = \frac{R_\infty R_e}{R_e - R_\infty} \quad (2)$$

Accordingly, the impedance of the equivalent circuit of FIG. 3A at an angular frequency ω, where ω=2π*frequency, is given by:

$$Z = R_\infty + \frac{R_0 - R_\infty}{1 + (j\omega\tau)} \quad (3)$$

where: $R_\infty$=impedance at infinite applied frequency
$R_0$=impedance at zero applied frequency=$R_e$ and,
τ is the time constant of the capacitive circuit.

However, the above represents an idealised situation which does not take into account the fact that the cell membrane is an imperfect capacitor. Taking this into account leads to a modified model in which:

$$Z = R_\infty + \frac{R_0 - R_\infty}{1 + (j\omega\tau)^\alpha} \quad (4)$$

where: α has a value between 0 and 1 and can be thought of as an indicator of the deviation of a real system from the ideal model.

Figure 3B:
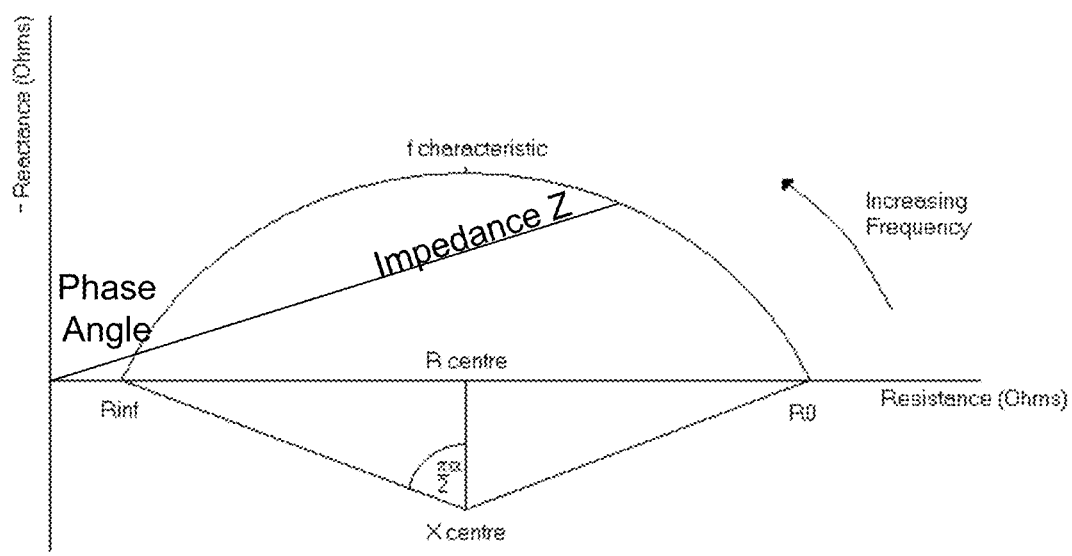
FIG. 3B is an example of a locus of impedance known as a Wessel plot.

An example of the typical multi-frequency impedance response is shown in FIG. 3B. As frequency increases, the reactance increases to a peak at the characteristic frequency and then decreases while the resistance continually decreases. This results in a circular locus with the centre of the circle below the x axis, as shown.

The values of impedance parameters $X_c$, $R_0$, $R_\infty$, $Z_c$ or α may be determined in any one of a number of manners such as by:
estimating values based on impedance measurements performed at selected respective frequencies;
solving simultaneous equations based on the impedance values determined at different frequencies;
using iterative mathematical techniques;
extrapolation from a plot of resistance against reactance for impedance measurements at a plurality of frequencies (a "Wessel plot" similar to that shown in FIG. 3B);
performing a function fitting technique, such as the use of a polynomial function.

For example, the Wessel plot is often used in BIS devices, which perform multiple measurements over a range of frequencies, such as from 1 kHz to 1000 kHz, using 256 or more different frequencies within this range. A regression procedure is then used to fit the measured data to the theoretical semi-circular locus, allowing values for $X_c$, $R_0$, $R_\infty$, $Z_c$ or α to be calculated. Alternatively, a circle fitting technique can be used in which three simultaneous equations representing the geometric relationships between points on a circle are solved to allow calculation of the radius (r) and the co-ordinates of the centre of the circle (i, j) as the three parameters which define the circle.

In one example, the frequencies used are in the range 0 kHz to 1000 kHz, and in one specific example, four measurements are recorded at frequencies of 25 kHz, 50 kHz, 100 kHz, and 200 kHz, although any suitable measurement frequencies can be used.

A further alternative for determining impedance parameter values such as $X_c$, $R_0$, $R_\infty$, $Z_c$ or $\alpha$ is to perform impedance measurements at a single frequency, and use these as an estimate of the parameter values. In this instance, measurements performed at a single low frequency (typically less than 50 kHz) can be used to estimate $R_0$, measurements at a single high frequency (typically more than 100 kHz) can be used to estimate $R_\infty$, allowing a value of $R_i$ to be determined using equation (2) above.

The above described equivalent circuit models the resistivity as a constant value and does not therefore accurately reflect the impedance response of a subject, and in particular does not accurately model the change in orientation of the erythrocytes in the subject's blood stream, or other relaxation effects. To more successfully model the electrical conductivity of the human body, an improved CPE based model may alternatively be used.

In any event, it will be appreciated that any suitable technique for determination of the parameter values such as $R_0$, $Z_c$, $R_\infty$, and $X_c$ may be used, hence allowing $R_i$ to be derived.

Accordingly, the above described arrangement allows the measuring device to be used with a number of different connectivity module types, with the measuring device processor performing the at least one impedance measurement at least in part depending on the connectivity module type of a connected connectivity module.

A number of further features will now be described.

In one example measuring device processor determines a connectivity module type of the connected connectivity module and in accordance with the determined connectivity module type, causes the at least one impedance measurement to be performed or processes a measured response signal to determine at least one impedance value indicative of a measured impedance. Accordingly, this allows the impedance measurement or analysis processes to be controlled based on the connectivity module type.

The connectivity module type can be determined in any suitable manner In one example, this is determined using one or more of a configuration of connections between the first and second connectors or a configuration of the second connector. For example, the first and second connectors can include a plurality of individual connections, with the connectivity module type being determined based at least in part on connections between individual connections of the second connector, created for example using jumpers or other similar arrangements. Alternatively, this could be based on a property of an electrical component electrically connected to the second connector, such as the resistance of a resistor coupled between respective connections on the second connector. Thus, the connectors could be configured, either based on respective interconnections, or through components coupled thereto, so that the connectivity module type can be determined automatically based on the configuration of the connectors.

Alternative mechanisms could also be used for determining a connection module type, such as by having the measuring device include a contact switch that is selectively actuated by the connectivity module housing when the measuring device and connectivity module are connected, so that a different switch position or different switch is actuated for different connectivity module types.

Additionally, and/or alternatively, the measuring device processor could determine an identifier associated with the connectivity module and determine the connectivity module type using the identifier. In this example, the connectivity module could include a memory, with the measuring device processor retrieving the identifier from the memory via a wireless connection or via the first and second connectors. The identifier could be in the form of a unique alphanumeric code or the like, and could include a portion that is indicative of a connectivity module type, and an additional serial number or the like, allowing not only the module type to be determined, but also allowing each module of a given type to be distinguished, which can be useful for calibration or tracking individual modules.

As a further alternative, instead of determining a connectivity module type, the measuring device processor could retrieve instructions from a memory in the connectivity module, via a wireless connection or the first and second connectors and then cause impedance measurements to be performed in accordance with the instructions. In this instance, instructions corresponding to measurements that can be performed are stored on the connectivity module itself, allowing these to be simply accessed and used as required.

Additionally, as mentioned above, the measuring device processor may determine the connectivity module type and then pass this information to a remote processing system, such as a client device, allowing the client device to determine the impedance measurements that can be performed in a similar manner.

As previously mentioned, the measuring device processor typically determines at least one impedance value indicative of at least one measured impedance using an indication of at least one drive signal applied to the subject and an indication of at least one measured response signal. Additionally however, the measuring device processor can also take into account calibration data stored in a memory. In this regard, the inherent electrical properties of the measuring device 110 and/or the connectivity module 120 can have an impact on the magnitude and/or phase of signals that are measured for a given impedance. For example, longer leads 122 between the electrodes 123, 124 and the second connector 121, can introduce additional resistances, leading to different voltages being recorded for the same impedance. Accordingly, calibration of the measuring device 110 and/or connectivity module 120 may be required in order to ensure that signals are accurately interpreted. Such calibration data can be established through measurement of reference impedances during a calibration process, and is taken into account when calculating the impedance, for example by modifying the resulting impedance or the phase and/or magnitude of measured signals prior to the impedance being measured.

In one example, the calibration data includes first calibration data specific to the measuring device and second calibration data specific to the connectivity module. In this instance, the measuring device processor 112 might determine the calibration data to be used based on a connectivity module type and/or a connectivity module identifier, so that the calibration data is specific to the type and/or particular connectivity module being used.

In one example, the measuring device processor 112 selects one of a number of calibration data sets stored in a memory, allowing the measuring device processor 112 to select and use the most appropriate calibration data, depending on the connected connectivity module and/or the impedance measurement being performed. In this regard, it will be appreciated that different calibration data might be required for example for high versus low frequency measurements.

The first and second connectors can be of any appropriate form but typically include multi-pin plug and a corresponding multi-pin socket connectors. In one example further physically separate connectors could also be provided, for example to allow for connection of different components. Thus, the first and second connectors could be used to connect the signal generator and/or sensor to the electrodes, with connections for indicators, such as LEDs, speakers or the like, being via different connectors, which can help avoid interference or the like.

The measuring device housing and connectivity module housing are typically configured to physically interconnect when the measuring device is connected to the connectivity module, for example using a clip-fit, friction-fit, interference-fit, magnetic coupling or the like.

The electrodes can be mounted on the connectivity module housing and/or coupled to leads extending from the connectivity module housing. It will be appreciated that this will depend on the intended usage, and specific examples will be described in more detail below.

In one example, the electrodes form part of at least one electrode sheet, which can include a substrate and conductive material defining each electrode, the conductive material being either impregnated in the substrate and/or printed on a surface of the substrate. In this example, the electrode sheet can include a connection tab extending from the substrate that allows a lead connector to be electrically coupled to the electrodes. In this regard, the tab can have electrical surface tracks provided thereon, allowing the tracks to electrically connect to contacts on the lead connector allowing for ease of connection.

In one example, the connectivity module 120 can include little more than the connector 121 and connections, such as leads 122, to the electrodes. However, alternatively, the connectivity module can include additional components, such as at least one buffer circuit coupled to each electrode, which is particularly important for high frequency operation. Thus, for example, the signal generator and sensor provided in the measuring device could be in the form of an DAC and ADC respectively, with respective amplifiers being provided in the connectivity module. It will be appreciated from this that power may be required by the connectivity module in which case a power supply such as a battery could be provided in the connectivity module. This could be a separate power supply to that used in the measuring device, or alternatively a common power supply could be used with power being transferred between the measuring device and connectivity module via the first and second connectors as required.

In one example, the measuring device includes a respective signal generator and/or sensor for each electrode. For example, for a four channel device, the measuring device can include four signal generators, each being electrically connected to a respective drive electrode and four sensors, each being electrically connected to a respective sense electrode and wherein the measuring device processor selectively activates the at least one signal generators and sensors to thereby allow a respective impedance measurement to be performed.

However, alternatively, the measuring device 110 includes a switching unit, such as a multiplexer, for selectively electrically connecting the at least one signal generator and the at least one sensor to the first connector thereby allowing the at least one signal generator and the at least one sensor to be selectively connected to different electrodes. In this instance, the measuring device processor 112 controls the switching unit to thereby selectively electrically connect the at least one signal generator and the at least one sensor to respective electrodes thereby allowing a respective impedance measurement to be performed. It will also be appreciated that such a switching unit could alternatively be provided in the connectivity module, although this is generally undesirable as it leads to additional complexity of the connectivity module 120.

The measuring device 110 can be controlled remotely using a processing system, such as the client device 130. Nevertheless, the measuring device 110 typically includes at least some form of minimal input/output device, to allow for user interaction. In one example, this includes an input button that activates the measuring device and/or causes at least one impedance measurement to be performed. The measuring device can also include an indicator, such as an optical indicator, a multi-colour LED, speaker or the like, which can be used to indicate completion of an impedance measurement, performing of an impedance measurement or connection to a connectivity module and/or processing system.

The measuring device 110 typically includes an interface, such as a wireless interface, for example Bluetooth or the like, that allows the measuring device processor to communicate with a processing system using at least one of wired and wireless communications.

In this case, the system 100 can include a processing system 130, that determines at least one impedance measurement to be performed, causes the measuring device to perform the at least one impedance measurement and receives an indication of at least one impedance value from the measuring device, the at least one impedance value being indicative of a measured impedance. In one example, the measuring device processor 112 can communicate with the processing system 130 to determine the at least one impedance measurement to be performed and/or provide the indication of at least one impedance value to the processing system 130. Thus, this allows the processing system 130, which can be in the form of a computer system, smartphone, tablet or the like, to act as a user interface, allowing the measuring device to be controlled and allowing results of the impedance measurement process to be reviewed. This in turn reduces the hardware requirements of the measuring device 110, whilst still allowing a range of different functionality to be implemented. The processing system 130 could be remote from the measuring device and connectivity module, or alternatively could be integrated into the connectivity module, depending on the preferred implementation.

In one example, the processing system 130 can determine an impedance measurement process to be performed, the impedance measurement process including a sequence of impedance measurements and cause the measuring device processor to perform the sequence of impedance measurements. This allows the processing system to be used to cause a complex sequences of impedance measurements to be performed, based for example on sequences stored locally on the processing system. This allows the system to be configured for particular circumstances, whilst allowing the measuring device 110 to be generic in terms of functionality, thereby minimising hardware requirements.

The processing system can also process the at least one impedance measurement to determine at least one indicator indicative of a biological state of the subject. This can be used for example to create an indicator that is indicative of a status of the subject, such as a fluid level, body composition parameter, or the like, making results of the impedance measurement easier for users, such as clinicians, to understand.

In one example, the processing system displays a user interface allowing a user to select at least one impedance measurement to be performed, select an impedance measurement process to be performed, the impedance measurement process including a sequence of impedance measurements, view at least one impedance measurement and view at least one indicator indicative of a biological state of the subject. However, this is not essential, and any suitable approach can be used.

In one example of the above described arrangements, the measuring device processor 112 can determine at least one performable impedance measurement based on a connectivity module type of a connected connectivity module and provide an indication of this to the processing system, which then displays an indication of the at least one performable impedance measurement to a user, determines a selected performable impedance measurement in accordance with user input commands and causes the measuring device to perform the selected performable impedance measurement. Thus, the measuring device 110 can determine the impedance measurements that can be performed based on the connected connectivity module, with this information being used by the processing system 130 to display available impedance measurement processes, so that one of these can be selected by the user. It will also be appreciated that a similar technique can be used to select the type of analysis that can be performed allowing indicators indicative of a biological status, such as body composition, fluid levels or the like, to be determined.

Figure 4A:
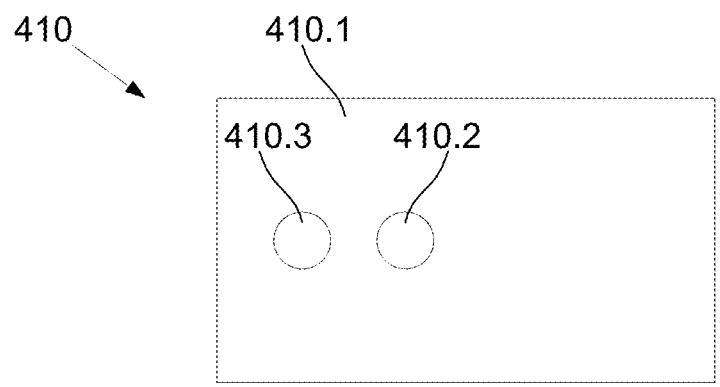
FIG. 4A is a schematic plan view of an example of a measuring device.
Figure 4B:
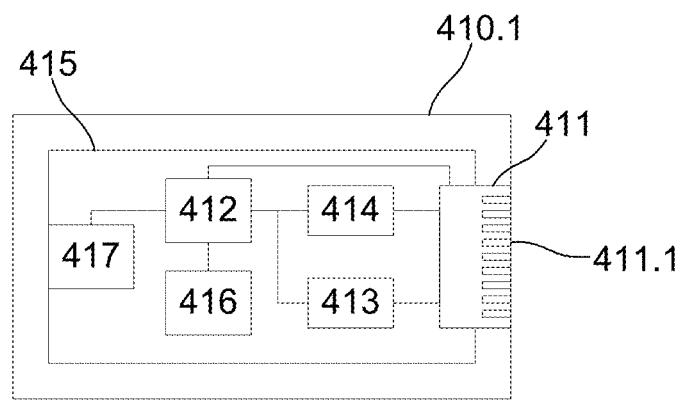
FIG. 4B is a schematic diagram showing internal components within the measuring device of FIG. 4A.
Figure 4C:
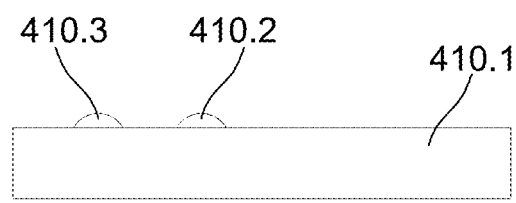
FIG. 4C is a schematic side view of the measuring device of FIG. 4A.
Figure 4D:
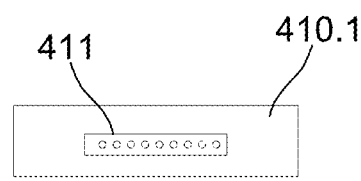
FIG. 4D is a schematic end view of the measuring device of FIG. 4A.

A specific example of a measuring device will now be described in more detail with reference to FIGS. 4A to 4B. In this example, similar reference numerals increased by 300 are used to refer to similar features to those shown in FIG. 1.

In this example, the measuring device 410 includes a housing 410.1 including an indicator 410.2 and an input 410.3. The indicator 410.2 can be of any suitable form, such as a multi-coloured LED, which can be used to indicate various status information such as whether the measuring device is turned on, it has a low charge, is connected to a connectivity module and/or a separate processing system, such as a client device, or is performing an impedance measurement. It will be appreciated that the status can be indicated through a combination of different colours, and/or different activations such as pulse sequences or the like. The input 410.3 is typically in the form of an input button, and can be used to activate the measuring device, and optionally to trigger an impedance measuring process. Again different functions could be initiated through multiple or timed button pushes, such as holding the input button down for a set time to turn the measuring device on or off.

The housing 410.1 typically contains a circuit board 415 on which the processor 412, signal generator 413, sensor 414 and connector 411 are mounted. The processor 412 is also coupled to a memory 416 and an optional external interface 417, which allows onward connectivity to a processing system, as will be described in more detail below.

The signal generator 413, sensor 414 and the measuring device processor 412 are coupled to the connector 411, which includes a number of individual connection pins or sockets 411.1. In this regard, the measuring device connector 411 could include pins or sockets with the complimentary sockets or pins being provided on the second connector in the connectivity module 120, as will be appreciated by persons skilled in the art.

It will be appreciated that the above represents a high level overview of the internal components of the measuring device and that in practice additional componentry can be used. For example, in practice, it is typical for the impedance measuring device to be a multichannel impedance measuring device allowing multiple different drive and response signals to be measured, and examples of these arrangements will now be described with reference to FIGS. 5A to 5D. For illustration, again similar reference numerals increased by 400 are used to refer to similar features to those shown in FIG. 1.

Figure 5A:
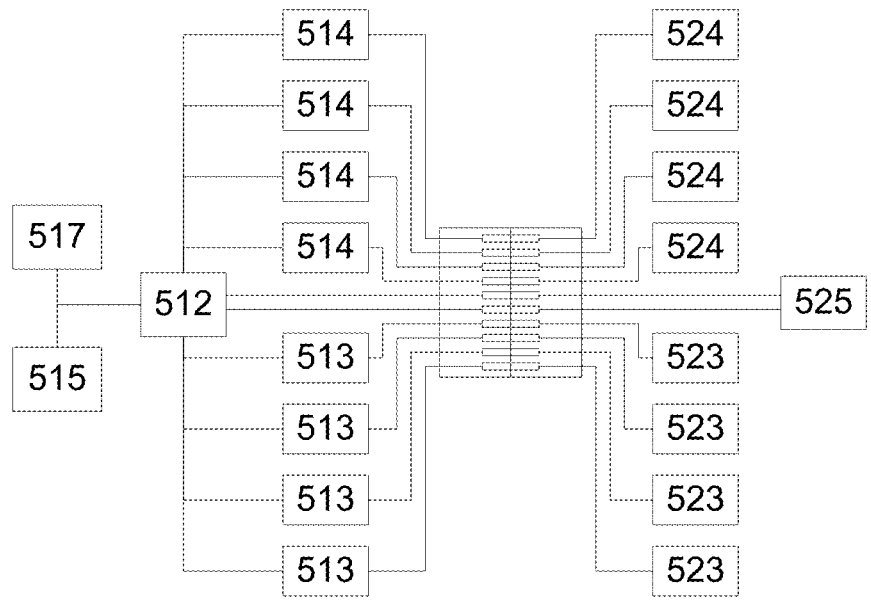
FIG. 5A is a schematic diagram of a further example of internal components of a measuring device.

In the example of FIG. 5A, the measuring device processor 512 is coupled to a plurality of signal generators 513 and sensors 514, with four of each being shown for the purpose of illustration. Each of the signal generators 513 are coupled to respective drive electrodes 523 via the connectors 511, 521, whilst the sensors 514 are coupled to respective sense electrodes 524 in a similar manner. Thus, in this example, a four channel device is provided with one-to-one connectivity between the signal generators 513 and sensors 514 and the respective electrodes 523, 524. It will be appreciated that this architecture could be expanded, for example to introduce further signal generators 513 and sensors 514, thereby allowing additional channels to be provided.

Additionally, in this example, one or more components 525 are connected to respective connector pins of the second connector 521, allowing the measuring device processor 512 to communicate with the components, for example to measure respective electrical properties, and/or retrieve data from a memory, thereby allowing a connectivity module type or identifier to be determined.

Figure 5B:
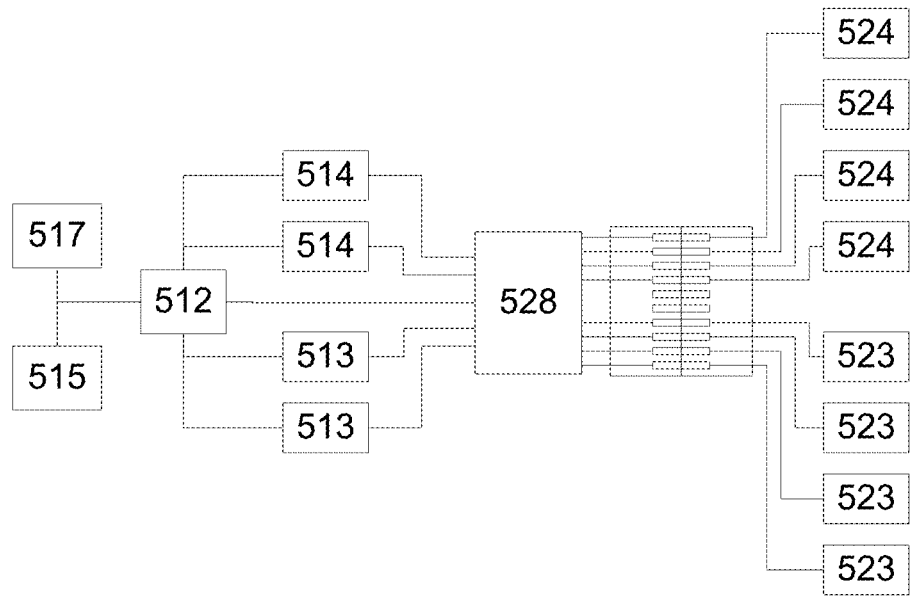
FIG. 5B is a schematic diagram of a second example of internal components of a measuring device.

In the alternative arrangement shown in FIG. 5B, two signal generators 513 and two sensors 514 are provided, coupled to a switching unit 518. The switching unit 518 is coupled to the first connector 511, allowing the signal generators 513 and sensors 514 to be selectively connected to two of four drive and four sense electrodes 523, 524. This allows the signal generators and sensors to be selectively connected to the electrodes 523, 524, so that different measurements can be performed. In particular, this allows differential drive and response signals to be applied/measured, with switching being performed to allow measurements to be made via different electrodes, for example provided at different locations on the subject.

Figure 5C:
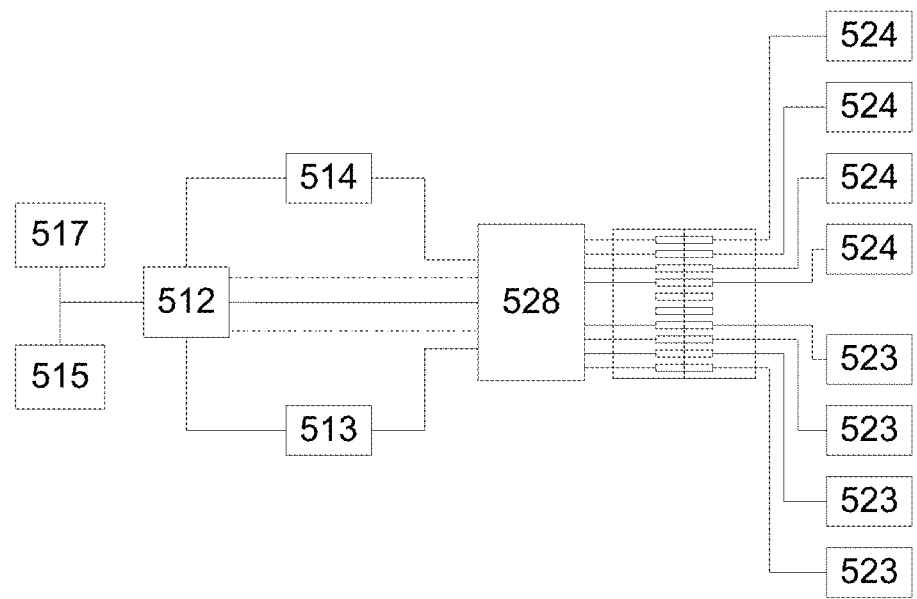
FIG. 5C is a schematic diagram of a third example of internal components of a measuring device.

In the example of FIG. 5C, only a signal generator 513 and single sensor 514 are provided, with the other signal generator and sensor being replaced by return paths (shown in dotted lines), so that the drive signals and response signals are applied/measured using a single ended asymmetrical configuration.

Figure 5D:
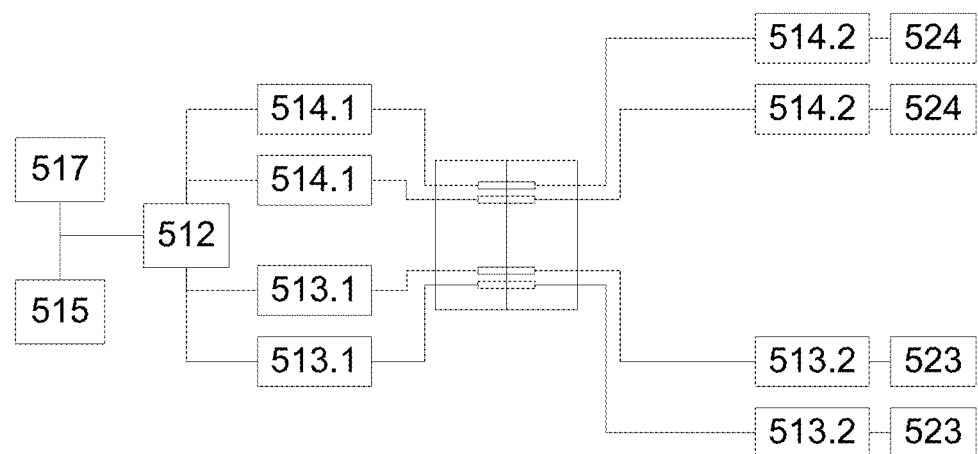
FIG. 5D is a schematic diagram of a fourth example of internal components of a measuring device.

In the example of FIG. 5D, the signal generators 513 and sensors 514 are split including some components in both the measuring device and connectivity module. In particular, in this example an DAC and ADC 513.1, 514.1 are provided as part of the measuring device with respective drive and sense buffer circuits 513.2, 514.2 being provided in the connectivity module. It will be appreciated that this is particularly useful for high frequency applications, reducing the lead length between the amplifier and the electrode, which in turn reduces the impact of noise.

Figure 6A:
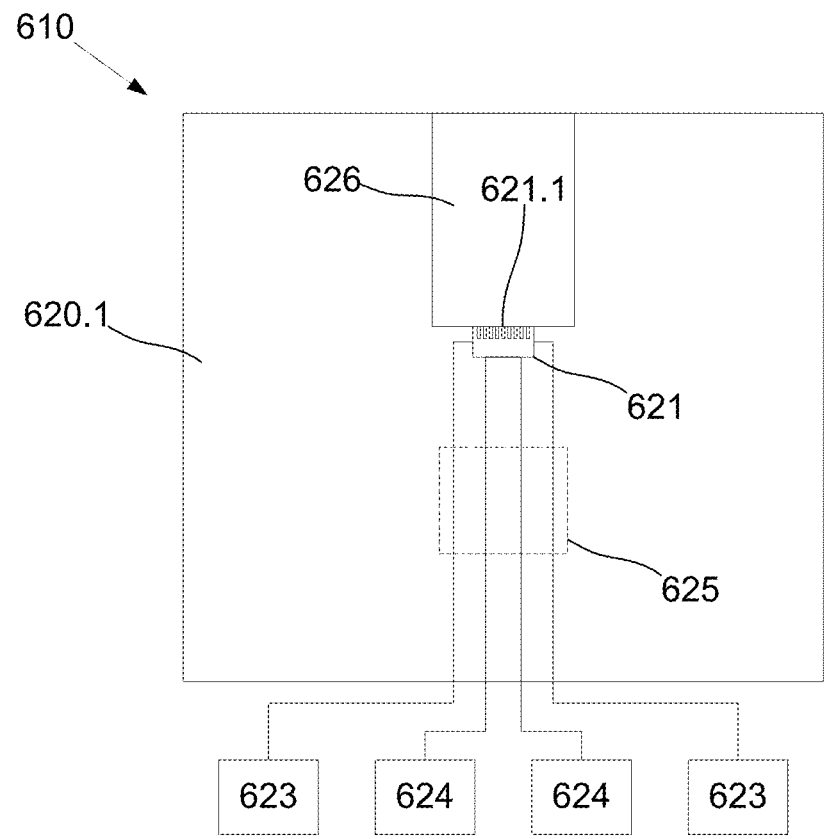
FIG. 6A is a schematic plan view of an example of a connectivity module.
Figure 6B:
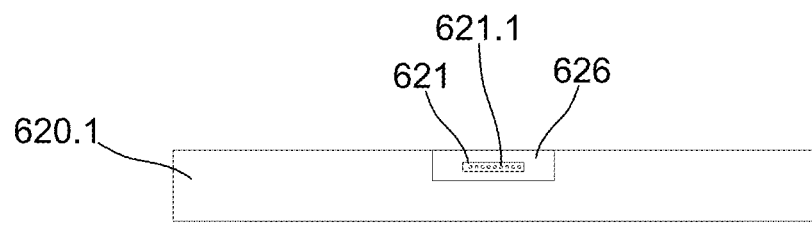
FIG. 6B is a schematic end view of the connectivity module of FIG. 6A.

An example of a connectivity module will now be described in more detail with reference to FIGS. 6A and 6B. In this example, similar reference numerals increased by 500 are used to refer to similar features to those shown in FIG. 1.

In this example, the connectivity module 620 includes a housing 620.1 containing the connector 621, which includes a plurality of sockets/pins 621.1 for connecting to the first connector 412 as previously described. The connectivity module 620 may include additional circuitry 625 which could be in the form of current or voltage buffers, or could include components whose properties are measured in order to determine connectivity module type. The housing 620.1 further includes a recess 626 into which the connectivity module can be placed allowing the first connector (not shown) and second connector 621 to interconnect.

Figure 7A:
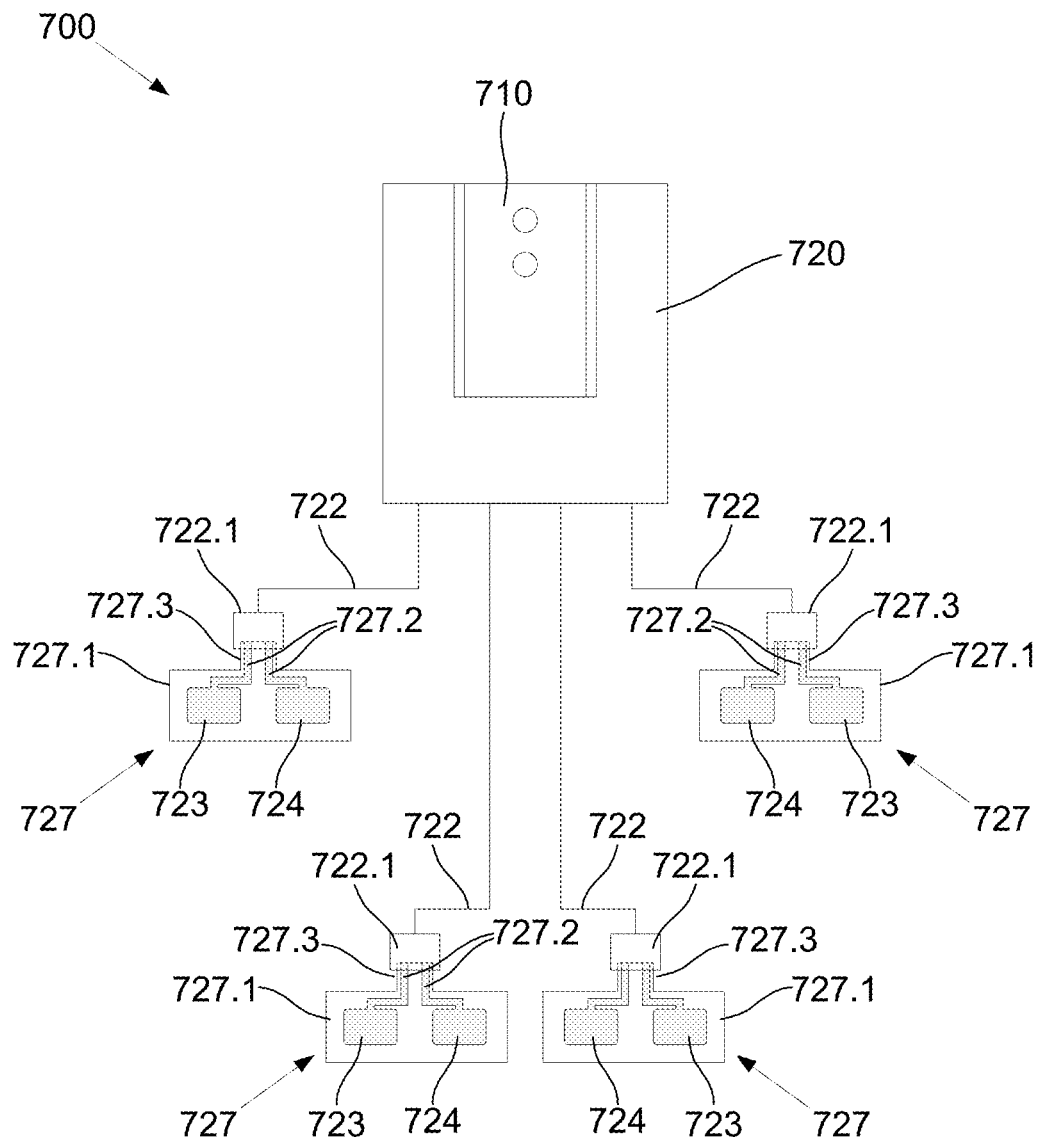
FIG. 7A is a schematic diagram of a first specific example of an impedance measuring system.

A specific example of a system including a first example connectivity module will now be described with reference to FIG. 7A. In this example, similar reference numerals increased by 600 are used to refer to similar features to those shown in FIG. 1.

In this example, the module housing 720 is coupled via leads 722 to respective electrode units 727, each of which includes a substrate 727.1 having a respective drive and sense electrode 723, 724 mounted thereon. The substrate 727.1 is typically a plastic sheet, such as an acetate sheet, with the electrodes being impregnated into the substrate surface, or printed thereon using conductive ink. Whilst filled areas could be used as the electrodes, this is not essential, and a grid pattern or the like could be used to reduce the amount of conductive material required to create each electrode.

Respective tracks 727.2 extend from the electrodes 723, 724 onto a tab 727.3, which acts to provide a mounting allowing a lead connector 722.1 to be coupled thereto. The lead connector is typically a clip that includes respective contacts that engage each track, thereby electrically connecting the electrodes 723, 724 to the lead 722, and hence the connector 721.

Figure 7B:
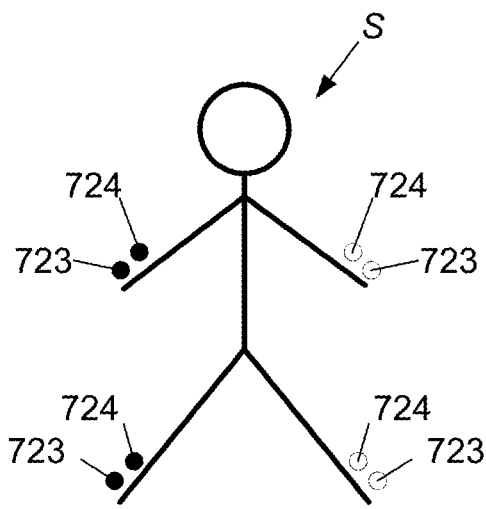
FIGS. 7B to 7D are schematic diagrams showing example electrode configurations in use for the measuring system of FIG. 7A.
Figure 7C:
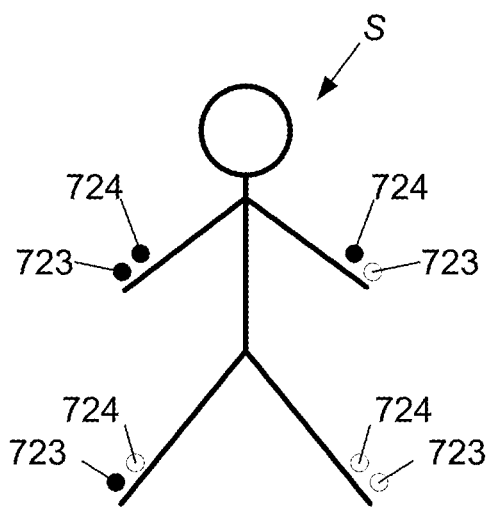
Figure 7D:
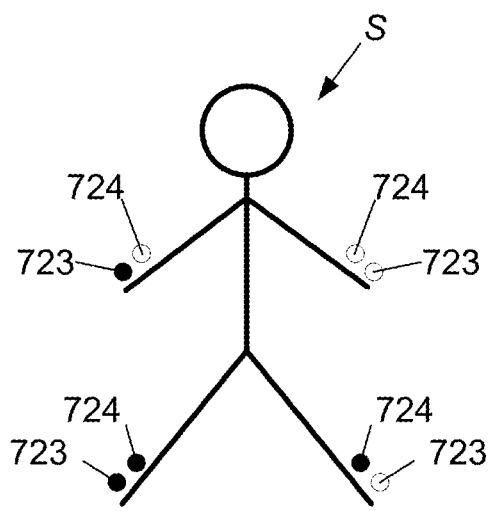

In use, each of the electrode units 727 can be attached to the subject, for example with respective units placed on each wrist and each ankle, and used to perform whole of body or segmental analysis. In this regard, example electrode arrangements are shown in FIGS. 7B to 7D, with active electrodes being shown filled and inactive electrodes shown as unfilled circles. In these examples, the configuration of FIG. 7B can be used for whole body measurements, whereas the arrangements of FIGS. 7C and 7D are used for the right arm and leg respectively.

A second example will now be described with reference to FIGS. 8A and 8B.

Figure 8A:
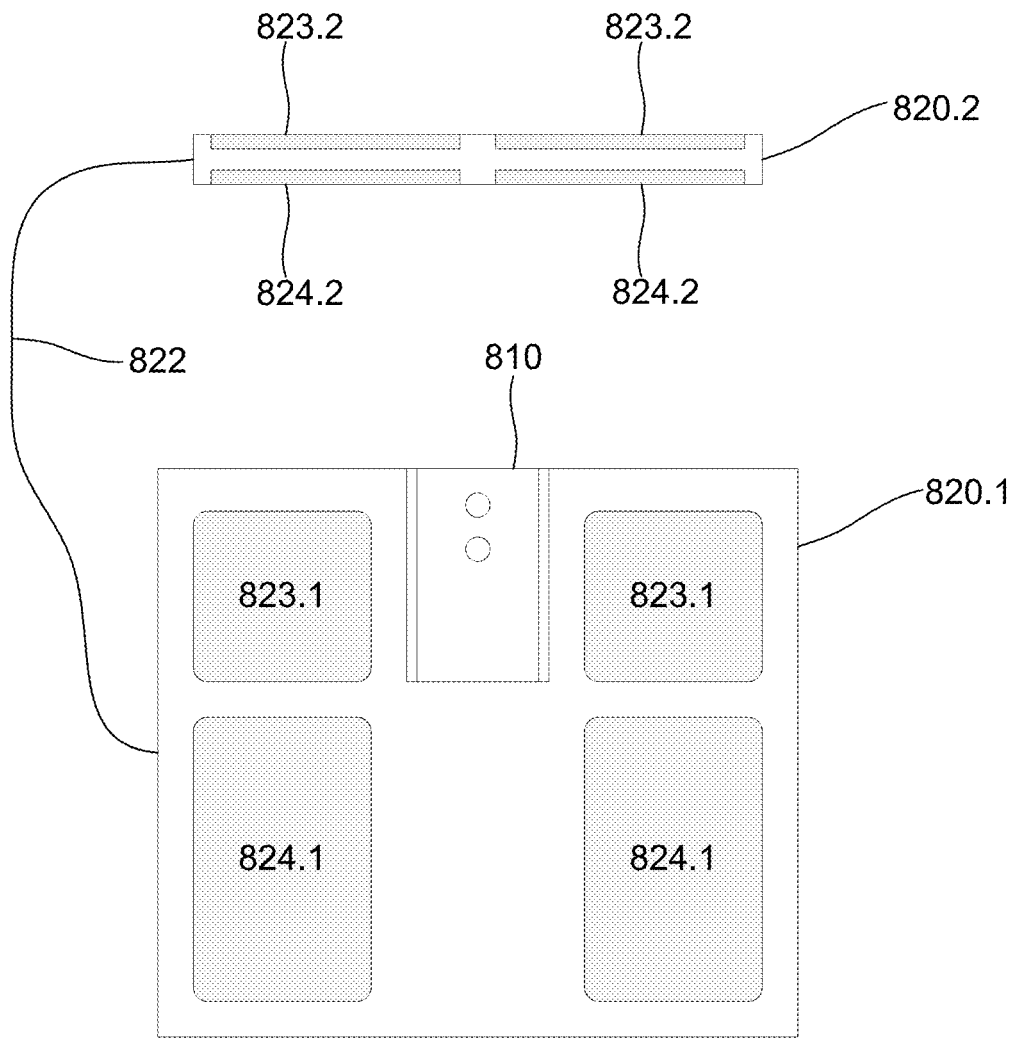
FIG. 8A is a schematic diagram of a second example of an impedance measuring system.
Figure 8B:
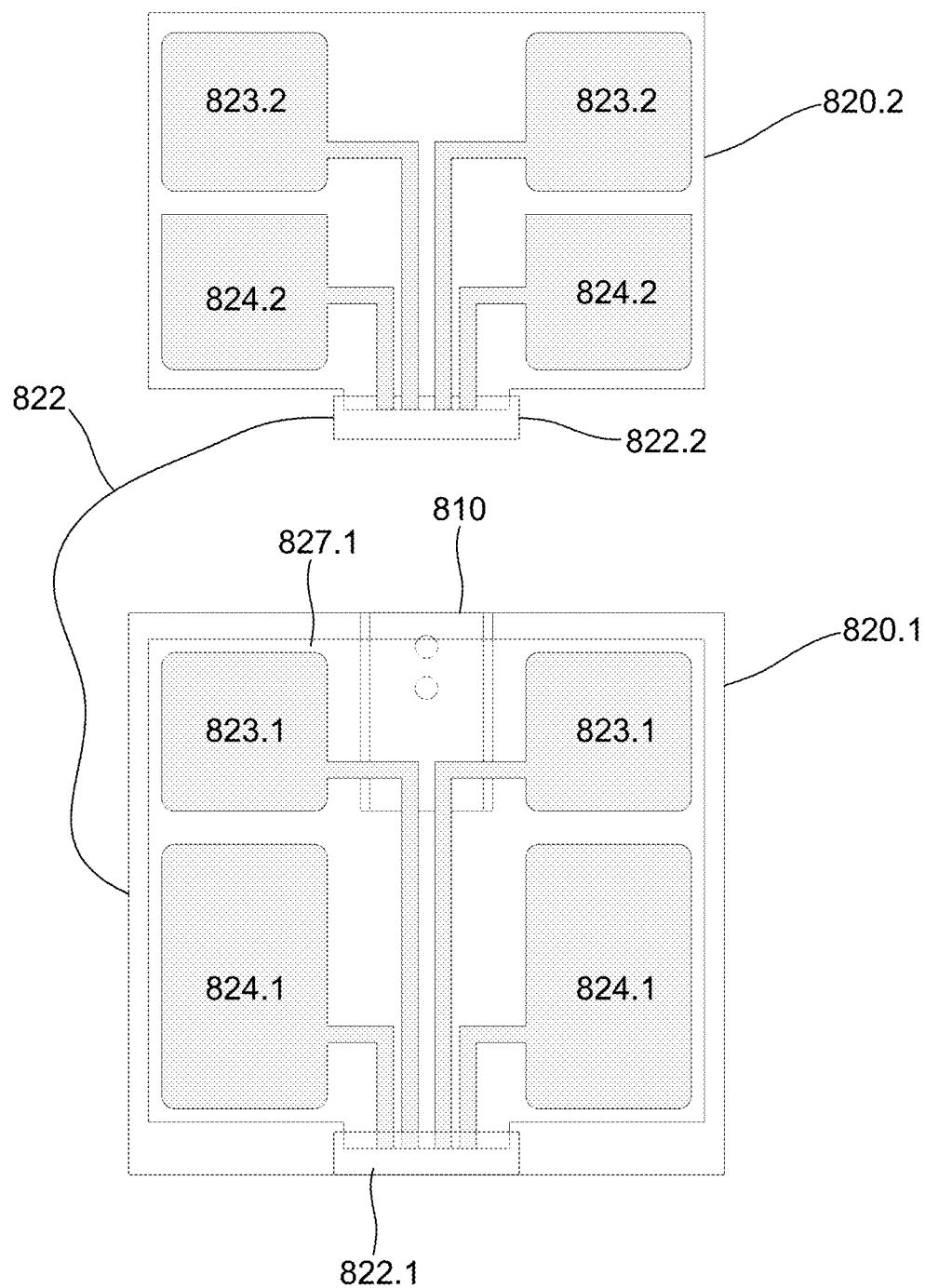
FIG. 8B is a schematic diagram of an example of an electrode sheet for the impedance measuring system of FIG. 8A.

In the example of FIG. 8A, the connectivity module includes first and second housings 820.1, 820.2 which are designed for use with the feet and hands respectively. In this example, the housing 820.1 is similar in form factor to a set of scales, and includes two spaced pairs of foot drive and sense electrodes 823.1, 824.1 forming footplates, on which a user can stand. Conversely, the second housing 820.2 is in the form of a tubular body that can be grasped by a user, and which includes two spaced pairs of semi cylindrical hand drive and sense electrodes 823.2, 824.2 mounted on opposing sides of the body so that these contacts the subject's hands when the subject grasps the housing 820.2. The hand drive and sense electrodes 823.2, 824.2 are coupled to the first housing 820.1 and hence the connector (not shown) via one or more leads 822. This arrangement allows the user to stand on the first housing 820.1 and grasp the second housing 820.2, allowing impedance measurements to be performed in a manner similar to that described above.

In one example, the foot electrodes 823.1, 824.1 could be in the form of metal plates mounted within the first housing 820.1. An alternative arrangement is shown in FIG. 8B. In this example, the foot electrodes 823.1, 824.1 could be provided on an electrode unit including a substrate 827.1 having respective electrodes 823.1, 824.1 printed thereon. Tracks 827.2 extend from the electrodes 823.1, 824.1 onto a tab 827.3, which acts to provide a mounting allowing a connector 822.1, typically mounted on the housing 820.1, to be coupled thereto, thereby electrically connecting the electrodes 823.1, 824.1 to the second connector (not shown).

A similar arrangement could also be used for the hand electrodes, with a sheet having the hand electrodes 823.2, 824.2 printed thereon. In this instance, the hand electrode sheet could be placed on a desk or table, whilst the connectivity module housing 820.1 is placed on the floor, allowing the impedance measurements to be performed whilst the subject is seated.

Figure 8C:
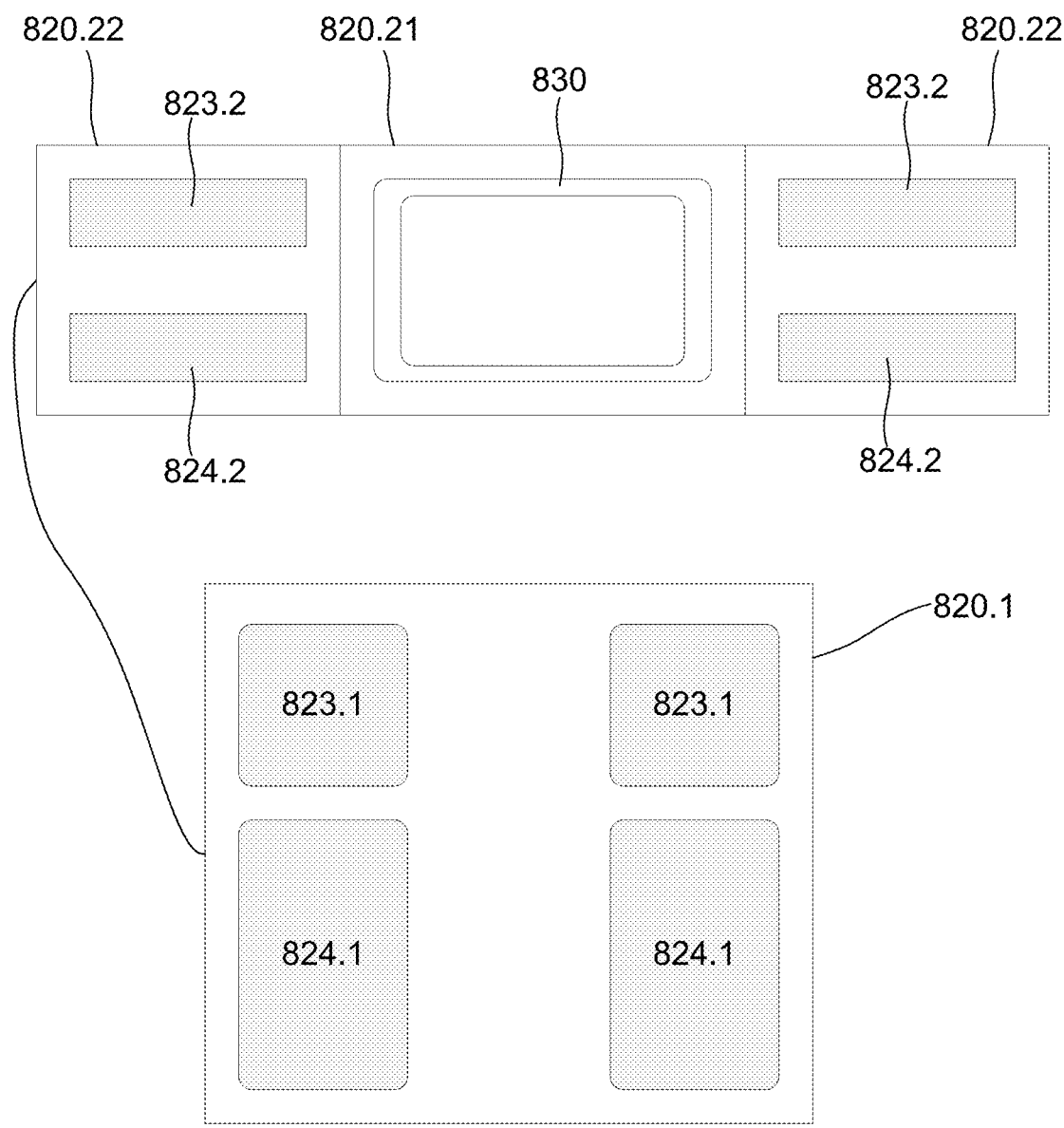
FIG. 8C is a schematic diagram of an example of an alternative impedance measuring system.
Figure 8D:
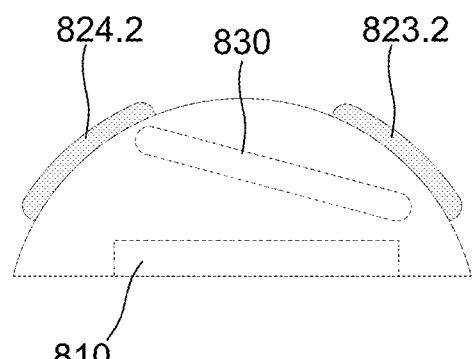
FIG. 8D is a schematic diagram end view of the second housing of the connectivity module of FIG. 8C.

A further example is shown in FIGS. 8C and 8D.

In this example, the connectivity module 820 again includes first and second housings 820.1, 820.2. The first housing 820.1 has a form factor similar to a set of scales, and includes two spaced pairs of foot drive and sense electrodes 823.1, 824.1 forming footplates, on which a user can stand. The second housing 820.2 is an elongate housing having three portions along its length, with a central rectangular portion 802.21 positioned between two outer semicylindrical portions 820.22. In this example, the outer semicylindrical portions 820.22 support curved electrode plates 823.2, 824.2 mounted on opposing sides of the body allowing the user to place their palms and fingers on the plates 823.2, 824.2. In this regard, the curvature of the surface assists with comfort and ensures good physical and hence electrical contact between the user's hands and the electrodes. Meanwhile the central portion can be used to support the measuring device 810, and also optionally a client device 830, such as a tablet or the like, which can be used to control the measurement process as will be described in more detail below.

It will be appreciated from this that a wide variety of connectivity modules could be provided, with these being used in different circumstances to allow respective types of impedance measurement to be performed, whilst still using a common measuring device.

Figure 9:
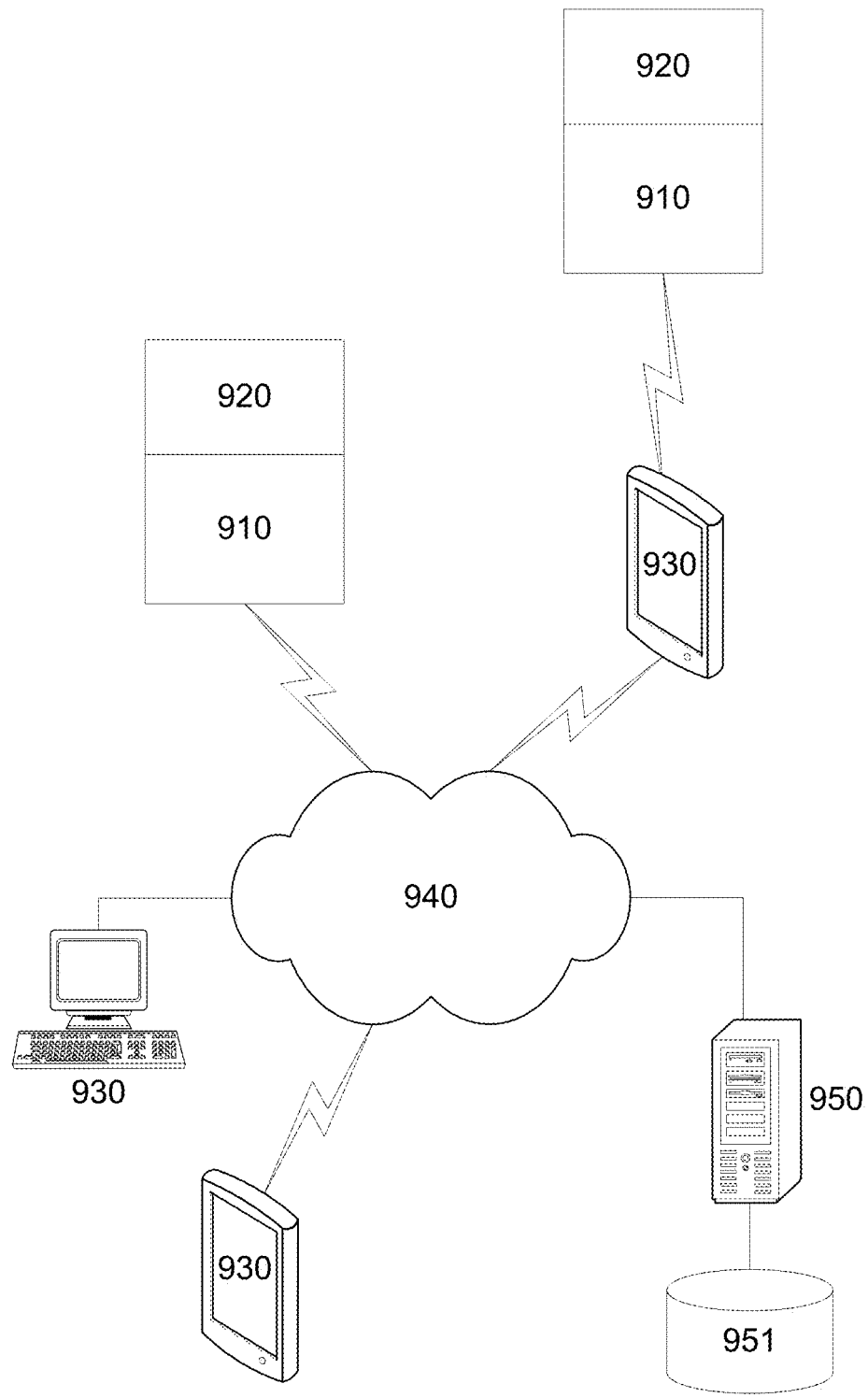
FIG. 9 is a schematic diagram of an example of a network based architecture.

In one example, the process is controlled by one or more processing systems, which may form part of a distributed architecture, an example of which will now be described with reference to FIG. 9.

In this example, the system 900 includes a first connectivity module 120.1 connected to a respective measuring device 110.1, which is in turn in communication with a processing system in the form of a client device 930. This allows the client device 930 to be used to control the measuring device 110.1, allowing impedance measurements to be performed based on the capabilities of the combined measuring device 110.1 and connectivity module 120.1.

The client device 930 may also be coupled via a communications network 940 to one or more other client devices and/or a processing system, such as a server 950. This allows results to be provided to other client devices 930 and/or the server 950, allowing these to be viewed remotely by third parties, such as clinicians, or the like.

Alternatively, as shown by a second connectivity module 120.2 and corresponding measuring device 110.2, the measuring device could be connected directly to the communications network 940, allowing this to be controlled by a remote client device 930 or the server 950 in a similar manner. Thus, it will be appreciated that the client device 930 or server 950 could connect to measuring devices 110 via an intervening communications network, and direct connection is not essential.

The communications network 940 can be of any appropriate form, such as the Internet and/or a number of local area networks (LANs) and provides onward connectivity to one or more client devices 930 and the server 950, which is in turn coupled to a database 951. It will be appreciated that this configuration is for the purpose of example only, and in practice the client devices 930 and servers 950 can communicate via any appropriate mechanism, such as via wired or wireless connections, including, but not limited to mobile networks, private networks, such as an 802.11 networks, the Internet, LANs, WANs, or the like, as well as via direct or point-to-point connections, such as Bluetooth, or the like.

Whilst the server 950 is a shown as a single entity, it will be appreciated that the server 950 can be distributed over a number of geographically separate locations, for example by using processing systems and/or databases 951 that are provided as part of a cloud based environment. Thus, the above described arrangement is not essential and other suitable configurations could be used.

Figure 10:
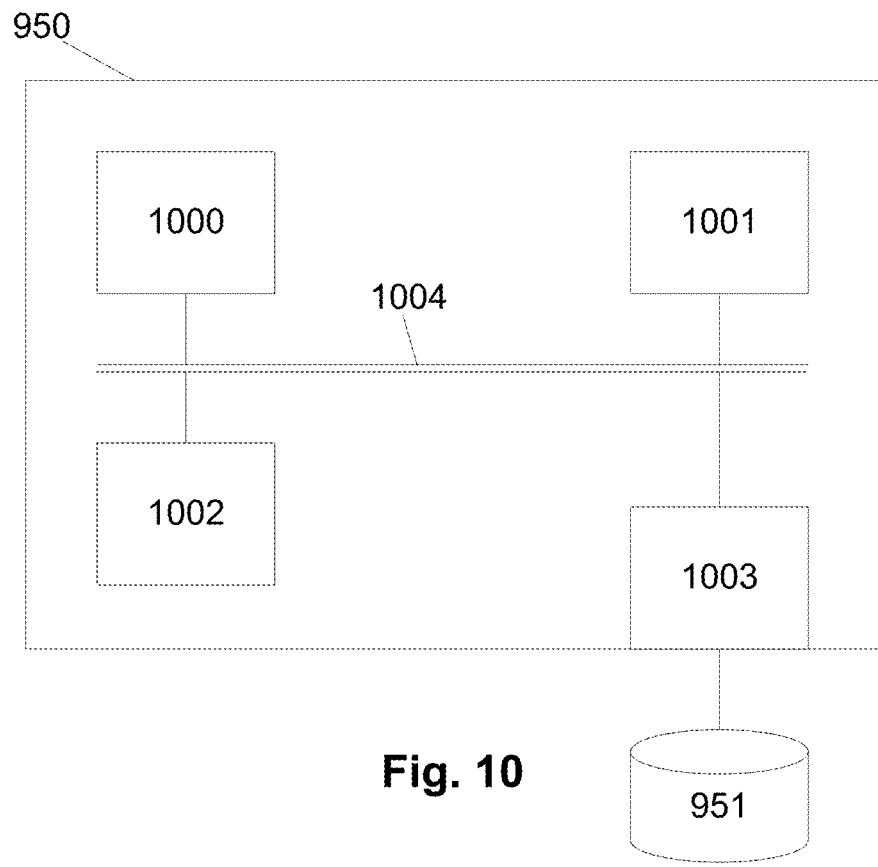
FIG. 10 is a schematic diagram of an example of the server of FIG. 9.

An example of a suitable server 950 is shown in FIG. 10. In this example, the server includes at least one microprocessor 1000, a memory 1001, an optional input/output device 1002, such as a keyboard and/or display, and an external interface 1003, interconnected via a bus 1004 as shown. In this example the external interface 1003 can be utilised for connecting the server 950 to peripheral devices, such as the communications networks 940, databases 951, other storage devices, or the like. Although a single external interface 1003 is shown, this is for the purpose of example only, and in practice multiple interfaces using various methods (eg. Ethernet, serial, USB, wireless or the like) may be provided.

In use, the microprocessor 1000 executes instructions in the form of applications software stored in the memory 1001 to allow the required processes to be performed, including communicating with the client devices 930, and optionally receiving, analysis and/or displaying results of impedance measurements. The applications software may include one or more software modules, and may be executed in a suitable execution environment, such as an operating system environment, or the like.

Accordingly, it will be appreciated that the server 950 may be formed from any suitable processing system, such as a suitably programmed client device, PC, web server, network server, or the like. In one particular example, the server 950 is a standard processing system such as an Intel Architecture based processing system, which executes software applications stored on non-volatile (e.g., hard disk) storage, although this is not essential. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement. Accordingly, whilst the term server is used, this is for the purpose of example only and is not intended to be limiting.

Figure 11:
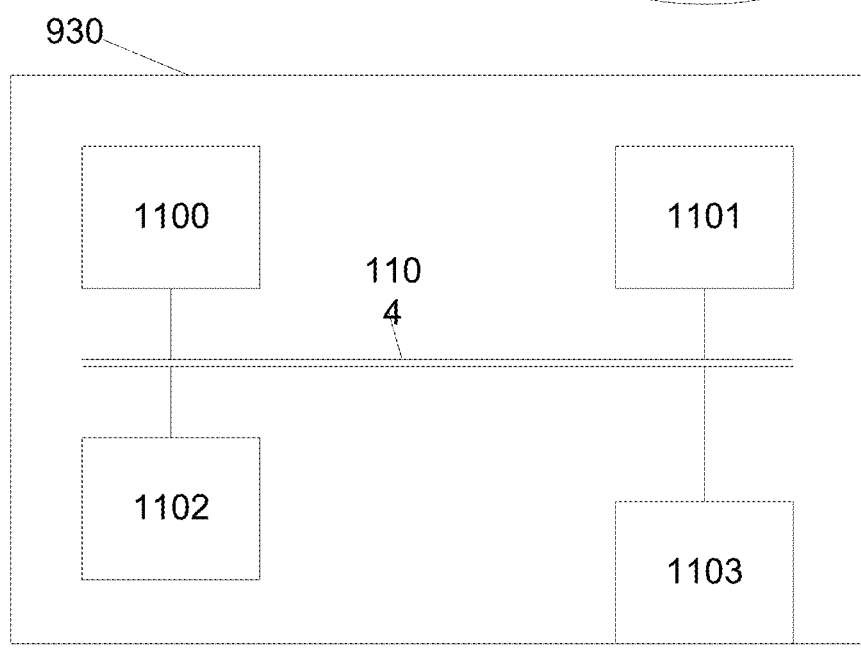
FIG. 11 is a schematic diagram of an example of a client device.

As shown in FIG. 11, in one example, the client device 930 includes at least one microprocessor 1100, a memory 1101, an input/output device 1102, such as a keyboard and/or display, and an external interface 1103, interconnected via a bus 1104 as shown. In this example the external interface 1103 can be utilised for connecting the client device 930 to peripheral devices, such as the communications networks 940, databases, other storage devices, or the like. Although a single external interface 1103 is shown, this is for the purpose of example only, and in practice multiple interfaces using various methods (eg. Ethernet, serial, USB, wireless or the like) may be provided.

In use, the microprocessor 1100 executes instructions in the form of applications software stored in the memory 1101 to allow communication with the server 950, for example to allow for representations of the activity indicator to be viewed, and to receive alerts, or the like.

Accordingly, it will be appreciated that the client devices 930 may be formed from any suitable processing system, such as a suitably programmed PC, Internet terminal, laptop, or hand-held PC, and in one preferred example is either a tablet, or smart phone, or the like. Thus, in one example, the client device 930 is a standard processing system such as an Intel Architecture based processing system, which executes software applications stored on non-volatile (e.g., hard disk) storage, although this is not essential. However, it will also be understood that the client devices 930 can be any electronic processing device such as a microprocessor, microchip processor, logic gate configuration, firmware optionally associated with implementing logic such as an FPGA (Field Programmable Gate Array), or any other electronic device, system or arrangement.

Examples of the operation of the system for monitoring activity capabilities of a subject, will now be described in further detail. For the purpose of these examples it will also be assumed that users use the client devices 930 to control a measuring device 110, allowing impedance measurements to be performed. This is typically achieved by having the user interact with the system via a GUI (Graphical User Interface), or the like presented on the client device 930, which may be generated by a local application, or hosted by the server 950 and displayed via a suitable application, such as a browser or the like, executed by the client device 930. Actions performed by the client device 930 are typically performed by the processor 1100 in accordance with instructions stored as applications software in the memory 1101 and/or input commands received from a user via the I/O device 1102. Similarly, actions performed by the server 950 are performed by the processor 1000 in accordance with instructions stored as applications software in the memory 1001 and/or input commands received from a user via the I/O device 1002, or commands received from the client device 930.

However, it will be appreciated that the above described configuration assumed for the purpose of the following examples is not essential, and numerous other configurations may be used. It will also be appreciated that the partitioning of functionality between the measuring device 110, client devices 930, and servers 950 may vary, depending on the particular implementation.

Figure 12:
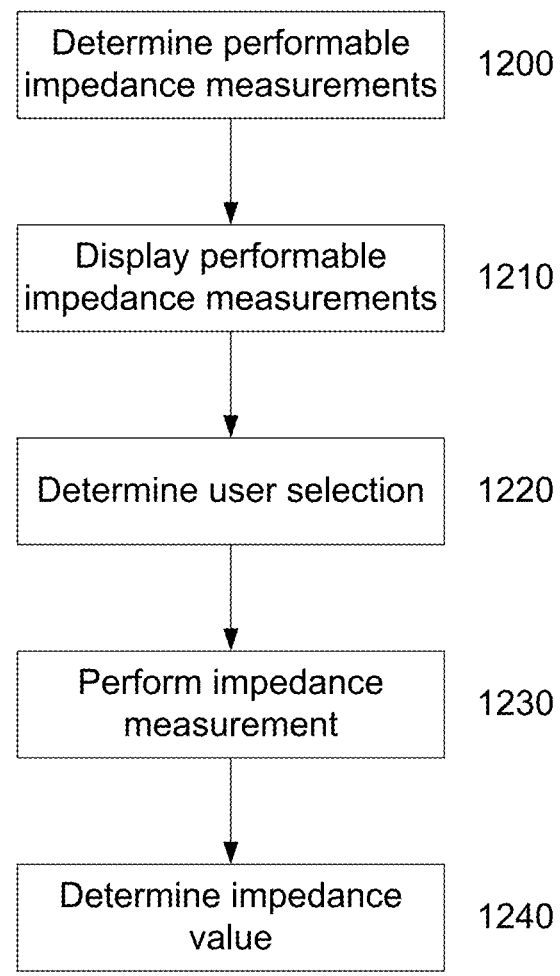
FIG. 12 is a flow chart of an example of an impedance measurement process.

An example of an impedance measurement process will now be described with reference to FIG. 12.

In this example, at step 1200 the client device 930 determines performable impedance measurements. This can be achieved in any suitable manner, but typically involves having the client device 930 query the measuring device 110 to determine what types of impedance measurements can be performed. The impedance measurements could include single impedance measurements, but more typically includes an impedance measurement process including a sequence of impedance measurements, allowing some form of indicator to be determined, such as an indicator indicative of respective fluid levels, body composition or the like.

The client device 930 displays an indication of the performable impedance measurements via a user interface at step 1210, allowing one of these to be selected by the user at step 1220. At step 1230, the client device 930 instructs the measuring device 110 causing the impedance measurement process to be performed in a manner substantially similar to that previously described. One or more impedance values are then determined by the measuring device 110 with these being returned to the client device 930 at step 1240. This allows the impedance value(s) to be displayed to the user, or alternatively used to determine an indicator, such as an indication of fluid level or the like, which can then be displayed and/or uploaded to the server 950 for storage or remote review.

Figure 13A:
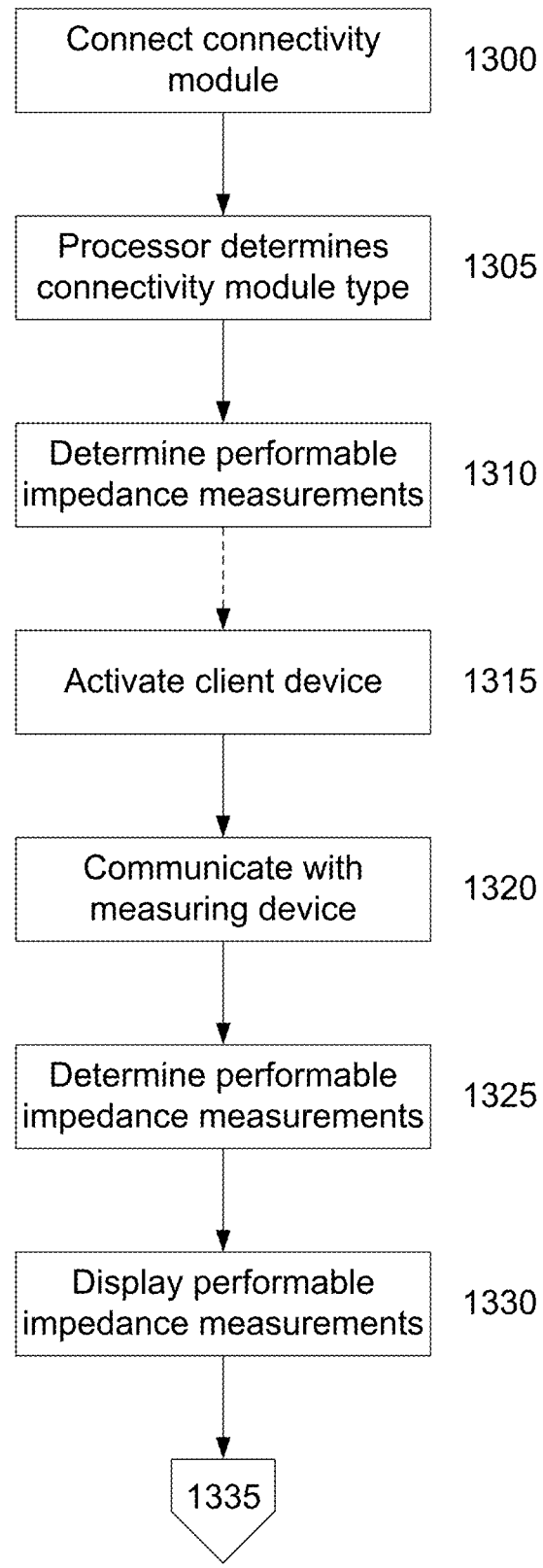
FIGS. 13A to 13C are a flow chart of a further example of an impedance measurement process.
Figure 13B:
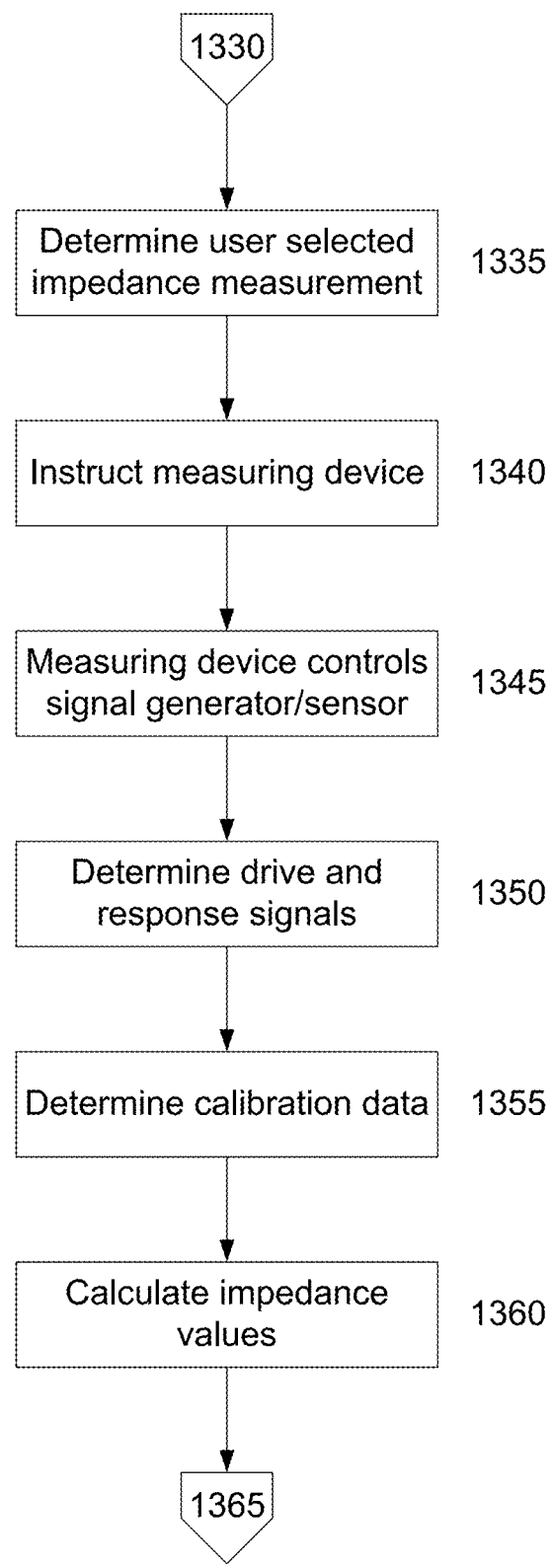
Figure 13C:
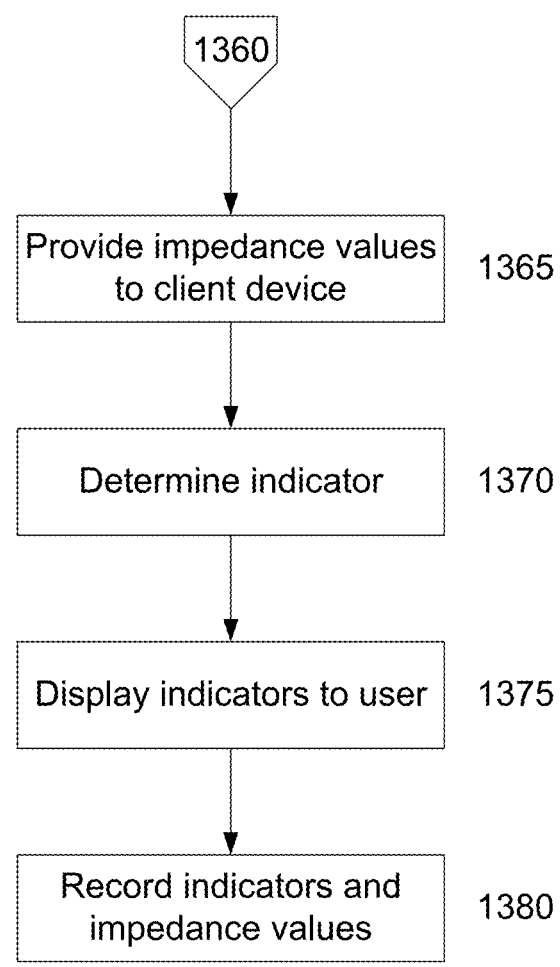
Figure 14A:
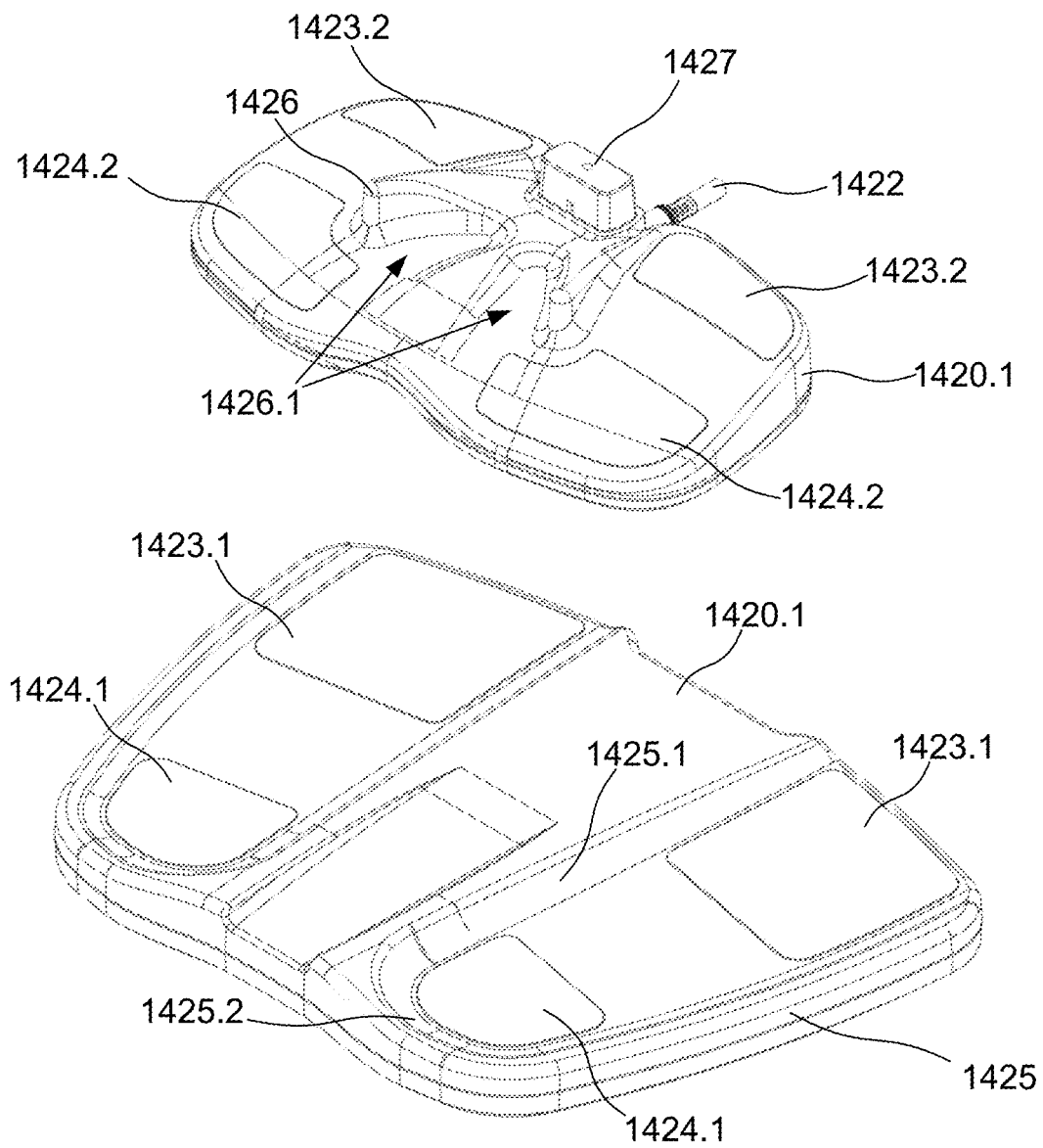
FIG. 14A is a schematic perspective view of a specific example of a connectivity module housing.
Figure 14B:
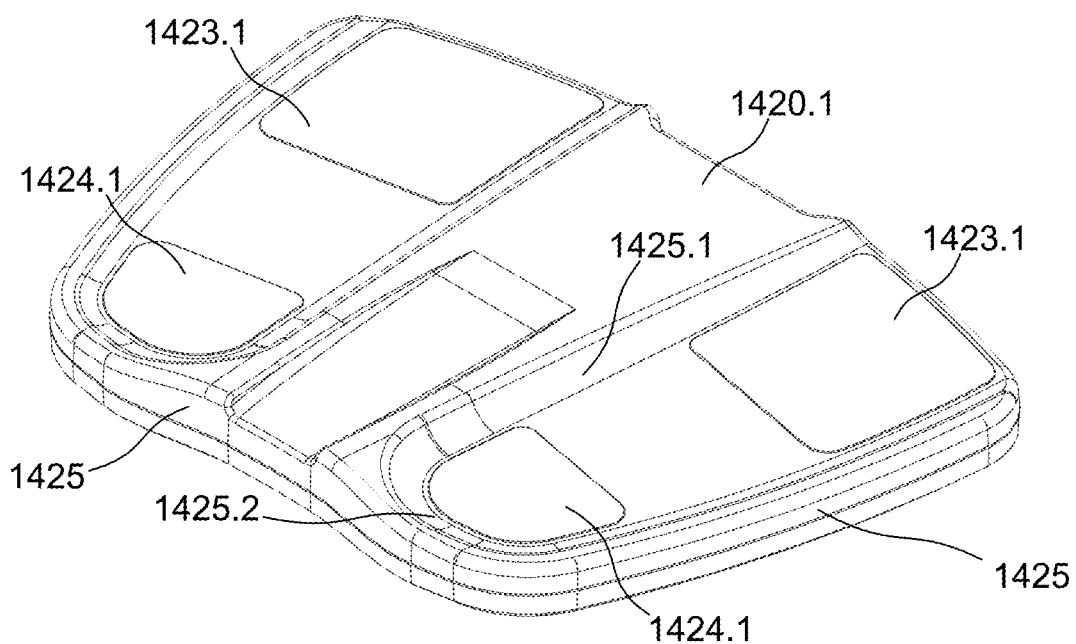
FIG. 14B is a schematic perspective view of a first housing of the connectivity module of FIG. 14A.
Figure 14C:
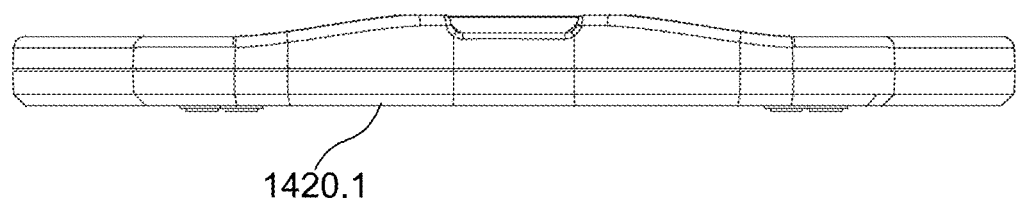
FIG. 14C is a schematic front view of the first housing of FIG. 14B.
Figure 14D:
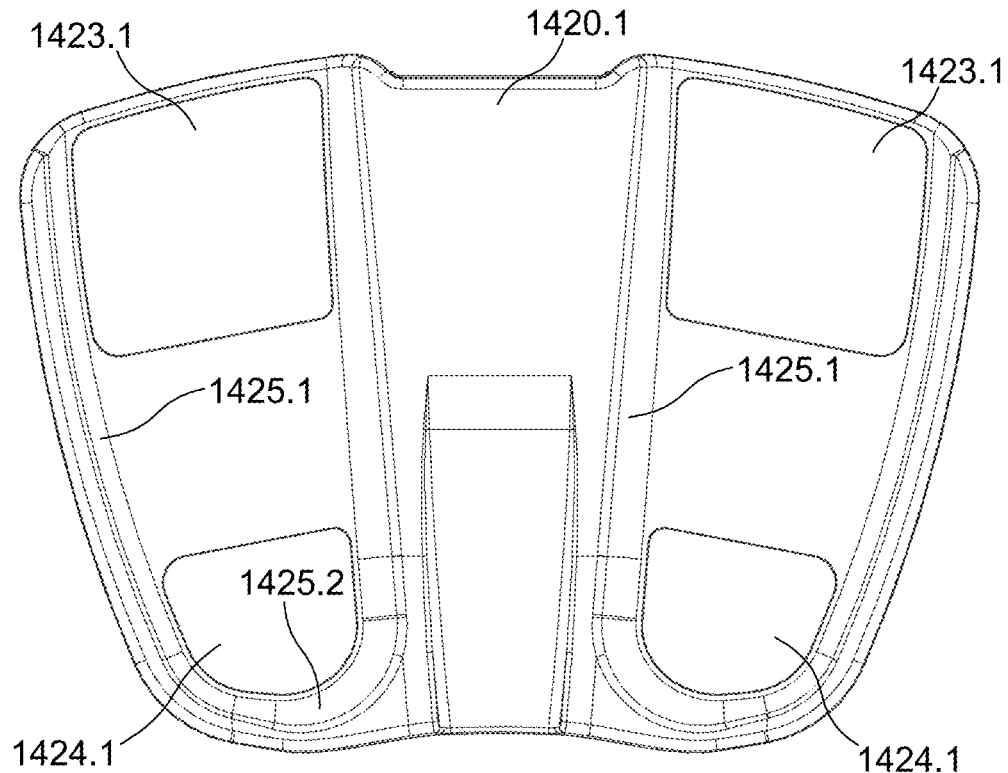
FIG. 14D is a schematic plan view of the first housing of FIG. 14B.
Figure 14E:
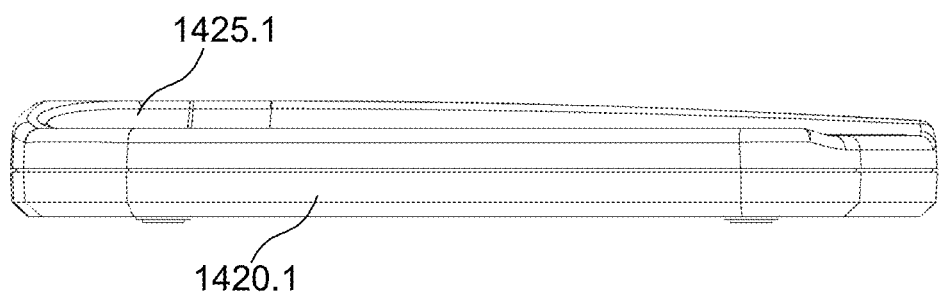
FIG. 14E is a schematic side view of the first housing of FIG. 14B.
Figure 14F:
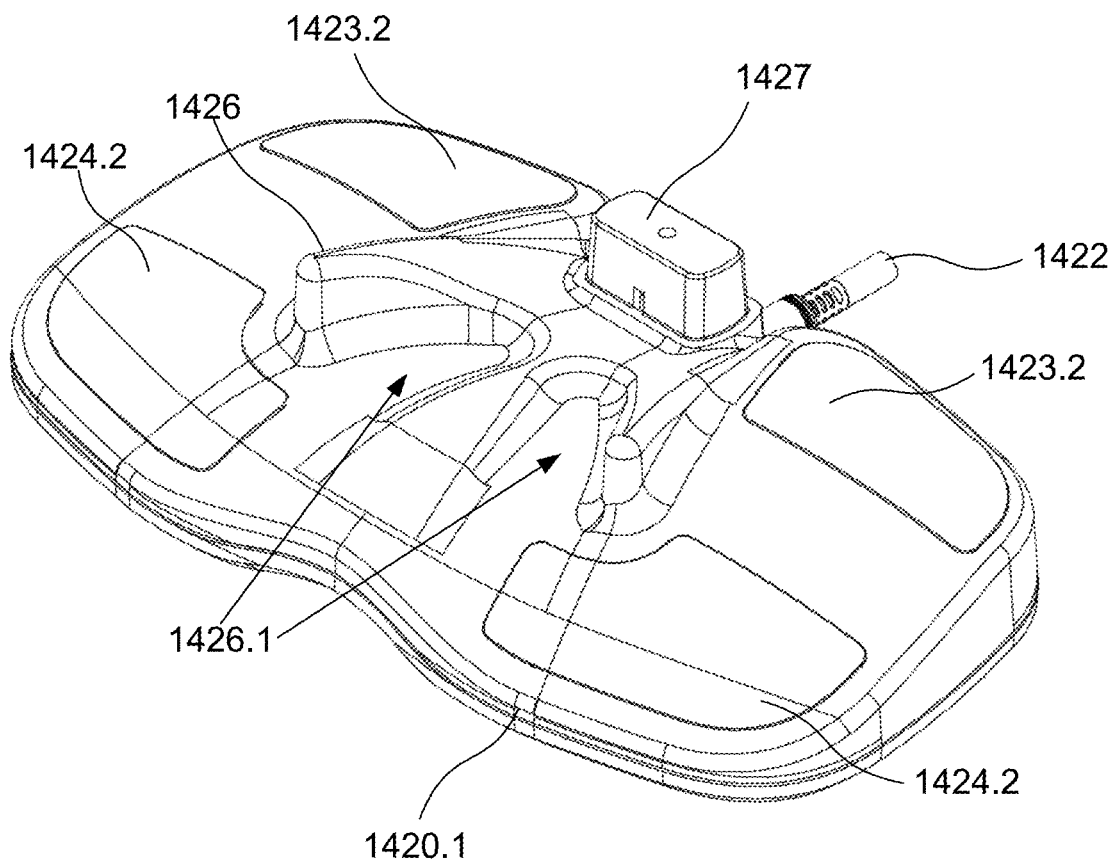
FIG. 14F is a schematic perspective view of a second housing of the connectivity module of FIG. 14A.
Figure 14G:
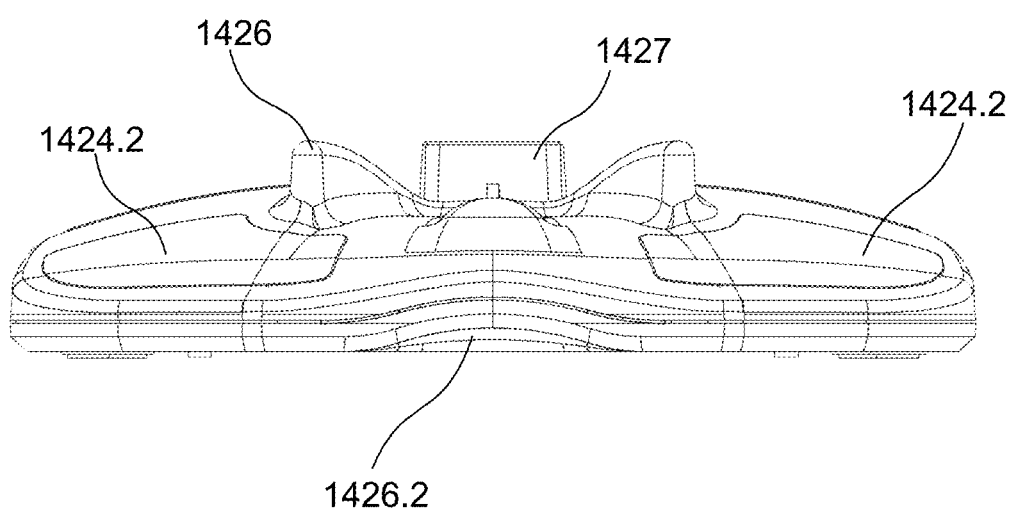
FIG. 14G is a schematic front view of the second housing of FIG. 14F.
Figure 14H:
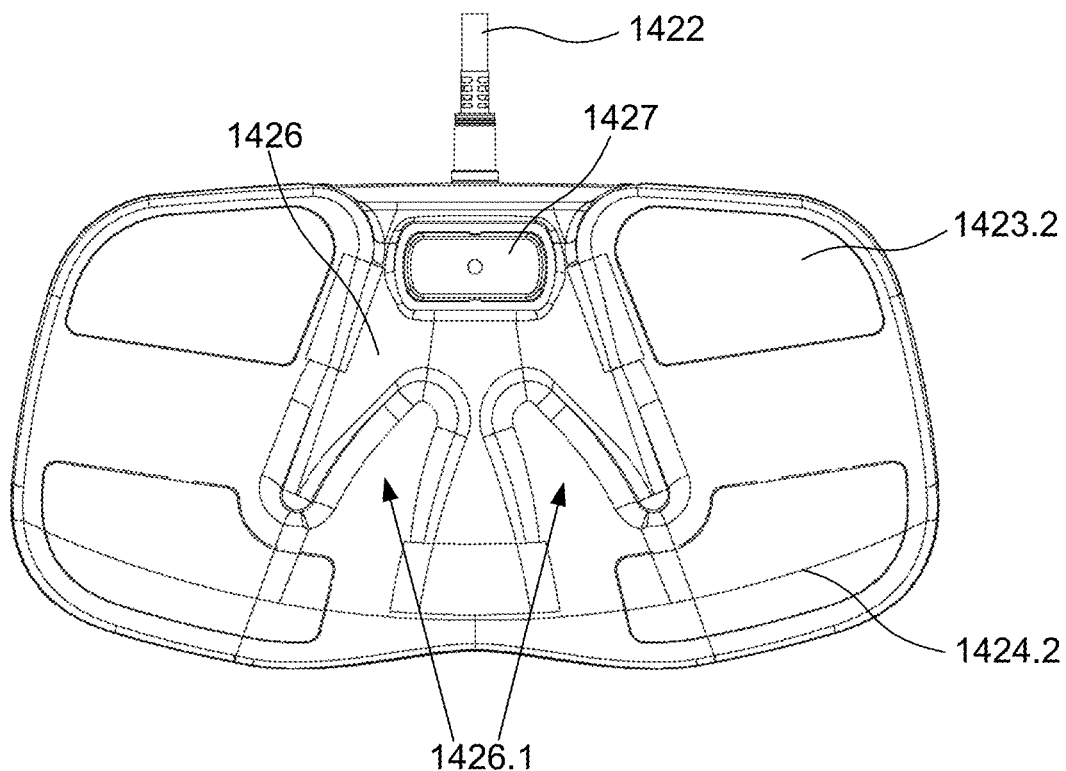
FIG. 14H is a schematic plan view of the second housing of FIG. 14F.
Figure 14I:
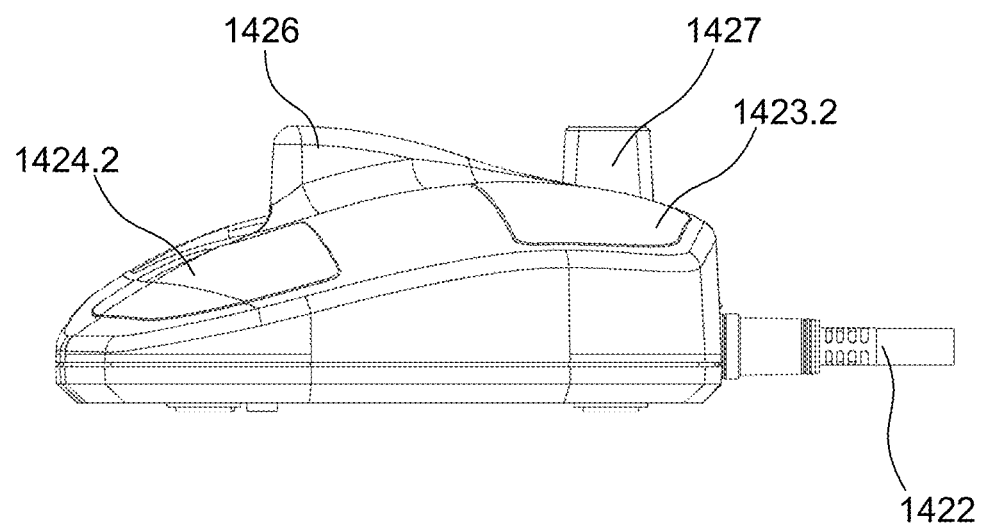
FIG. 14I is a schematic side view of the second housing of FIG. 14F.
Figure 14J:
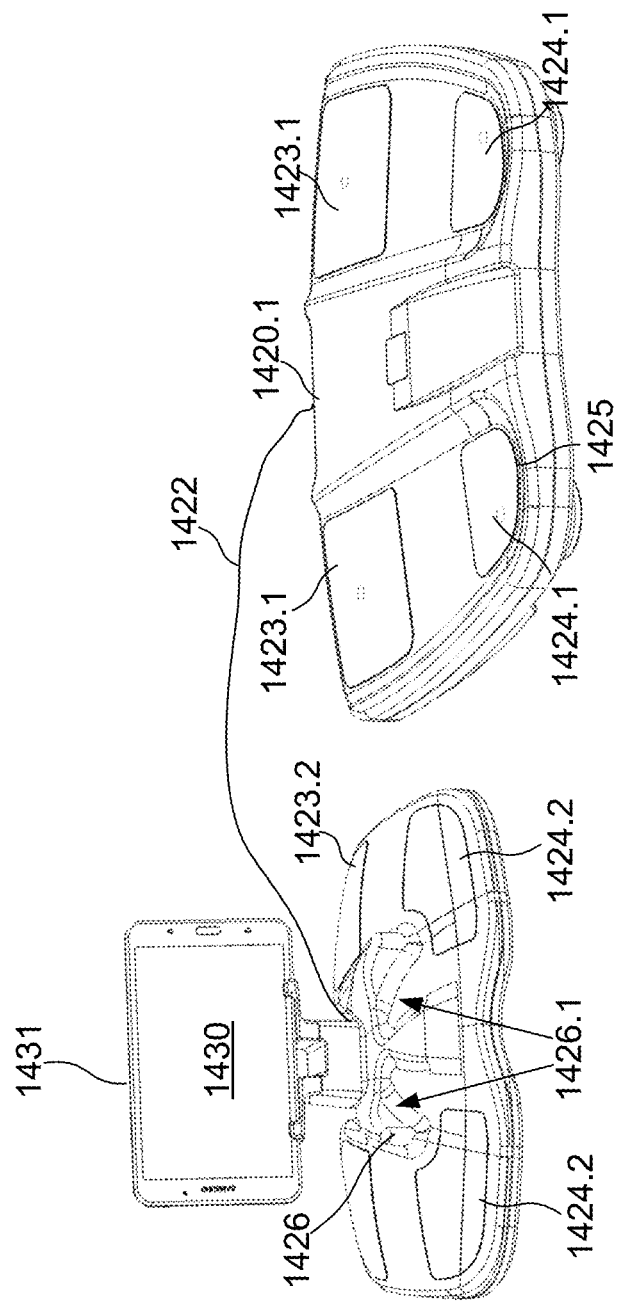
FIG. 14J is a rendering of an example of an impedance measuring apparatus incorporating the connectivity module of FIG. 14A.

A further example of an impedance measurement process will now be described with reference to FIGS. 13A to 13C.

In this example, at step 1300 the measuring device 110 is initially connected to a connectivity module 120, and activated, causing the measuring device processor to determine a connectivity module type of the connectivity module 120 at step 1305. This is typically performed by having the measuring device processor determine a connectivity module identifier or the like, allowing the measuring device processor to determine performable impedance measurements at step 1310. In this regard, the measuring device 110 can store a list of performable impedance measurements that can be performed for each type of module in onboard memory, allowing an indication of performable impedance measurements to be retrieved based on the connectivity module type. However, alternatively, the connectivity module type could be provided to the client device 930, allowing this to be performed by the client device 930.

At step 1315, a client device 930 is activated, with relevant software being activated, allowing the client device 930 to commence communicating with the measuring device 110 at step 1320. As part of this process, the measuring device and client device may need to be paired, for example undergoing a Bluetooth pairing process, or the like, depending on the manner in which the client device 930 and measuring device communicate. Alternatively a particular client device 110 previously paired with the client device 930 may need to be identified from a list of available devices, as will be appreciated by persons skilled in the art.

At step 1325, the client device 930 determines the performable impedance measurements from the measuring device 110, or receives an indication of the connectivity module type, allowing the performable impedance measurements to be determined locally. In any event, an indication of the performable impedance measurements is then displayed to a user at step 1330, for example in the form of a list of impedance measurement processes.

The user selects a performable impedance measurement at step 1335, causing the client device 930 to instruct the measuring device 110 to perform the impedance measurements at step 1340. This can include providing the measuring device 110 with an indication of particular impedance measurements to be performed, or could include providing instructions regarding the control of or settings for the signal generator, sensor and any switches. Additionally and/or alternatively, this could include uploading soft or firmware to the measuring device, allowing the measuring device 110 to operate as required.

At step 1345, the measuring device processor 112 controls the signal generator/sensor 113, 114, determining corresponding drive and response signals, applied or measured via respective drive and sense electrodes 123, 124, at step 1350. The measuring device processor 112 then determines calibration data at step 1355, with this typically being stored locally and accessed based on either the connectivity module type and/or connectivity module identifier. In this regard each type of connectivity module will typically have different electrical properties and these will need to be taken into account when performing impedance measurements. This is achieved by measuring drive and response signals for standardised electrical components with this then being used to generate calibration data which can be used in calculating impedance measurements. This could be performed for each type of module, and/or for each individual connectivity module, depending for example of the level of accuracy required for the calculated impedance values.

In any event, the calibration data is used together with the indication of the drive and corresponding response signals to calculate impedance values at step 1360, for example by modifying the measured drive and response signals to take into account device characteristics, and then using the modified signals to calculate the impedance.

Once impedance values have been calculated for each measurement performed, an indication of the impedance values being provided to the client device 930 at step 1365, allowing these to be used by the client device to determine one or more indicators at step 1370. This process can involve calculating impedance parameter values, such as $R_0$, $R_\infty$, or the like and then using these values to determine indicators, such as fluids levels including levels of extracellular and intracellular fluid, body composition parameters, such as fat free mass, or the like.

The determined indicator(s) and/or impedance values can then be displayed to the user at step 1375, via a suitable user interface with the indicators and impedance values being optionally stored at step 1380, for example by transferring these to the server 950 for storage in the database 951.

Accordingly, it will be appreciated that the above described arrangement allows the impedance measurement procedure to be controlled via a client device, such as a smartphone or tablet. This allows general processing of impedance measurements and control of the system to be performed using generic hardware, without unduly adding to the cost of the impedance measuring system.

A further specific example of a connectivity module and associated impedance measuring system is shown in FIGS. 14A to 14J.

In this example, the connectivity module again includes first and second housings 1420.1, 1420.2. The first housing 1420.1 has a form factor similar to a set of scales, and includes a generally rectangular body having two spaced pairs of foot drive and sense electrodes 1423.1, 1424.1 formed from spaced apart metal plates provided on an upper surface, thereby forming footplates on which a user can stand. The second housing 1420.2 has a similar form factor, including a generally rectangular body having two spaced pairs of hand drive and sense electrodes 1423.2, 1424.2 formed from spaced apart metal plates provided on an upper surface, thereby forming handplates on which a user can rest their hands.

The first housing 1420.1 includes a raised section 1425, defining a lip 1425.1 extending at least partially around each pair of foot drive and sense electrodes to thereby guide positioning of a subject's foot relative to the foot drive and sense electrodes in use. In particular, the raised lip 1425.1 includes a rear portion 1425.2 configured to engage at least a heel of the user. A similar effect is achieved for the second housing by having a raised portion 1426 positioned between each pair of hand drive and sense electrodes, the raised portion defining thumb recesses 1426.1 to thereby guide positioning of a subject's thumbs, with the crook of the thumb engaging the raised portion, and hence hands relative to each pair of hand drive and sense electrodes in use.

In this regard, it will be appreciated that whilst this will still allow for some minor variation in positioning between different individuals, for example due to different feet and hand sizes, this helps ensure that any given user's hands and feet are provided at a consistent position relative to the drive and sense electrodes each time the apparatus is used. This provides reproducible positioning, which in turn reduces variations between successive measurements that could be caused by changes in hand or foot position.

Additionally the second housing can include a processing system mounting 1427 that in use receives a support 1431, containing a processing system, such as a client device 1430 and in particular a tablet or other similar client device. In this regard, the mounting can include a rectangular plug extending upwardly from an upper surface of the housing, allowing a stem 1431.1 of the support to be seated thereon. This allows a tablet or other processing device to be suitably integrated into the connectivity module. In one example, the stem incorporates a pivoting arrangement, allowing the tablet to face towards or away from the subject, so that this can be used to allow an end user, or an operative, such as a clinican, to control the measurement process and view results.

The first and/or second housings can include keyhole mountings on an underside, allowing the first and/or second housings to be removably mounted to a pedestal. This can be used to provide a stand on arrangement, although this is not essential, and seated configurations could alternatively be used.

The second housing can also include a raised portion 1426.2 along one edge of an underside surface of the second housing, allowing a user to insert their fingers between the second housing and a support surface, to thereby more easily lift the second housing. Connector ports in a rear face of the first and second housing can also positioned beneath an overhang, to thereby reduce ingress of water drops into the connectors. Finally, the second housing can accommodate a USB port for charging a tablet or other processing device when coupled thereto.

In the above described arrangements, a single configuration of measuring device is adapted to be used with connectivity modules that provide onward connectivity to the subject. Different types of connectivity module can be used with the same measuring device, with the nature of the connectivity module being used to control the impedance measuring processes that can be performed. This allows a user to obtain a single measuring device and then use this with different connectivity modules, allowing different measurements to be performed. This reduces the complexity of the measuring device, and allows a single configuration of measuring device to be used in wide range of scenarios. Additionally, this allows users to only acquire connectivity modules that are relevant to measurements that are to be performed, avoiding the need to acquire unnecessary hardware. Finally, this also allows the connectivity modules to be customised for the particular measurements that are to be performed, which in turn helps ensure the electrode configuration is optimised for the particular measurements being performed.

In the above described arrangements, the measuring device is provided in a measuring device housing that is separate to the connectivity module housing. This is beneficial in terms of facilitating use of a single measuring device with multiple different connectivity modules, particularly in terms of allowing for measuring device handling to be performed when attaching or detaching the measuring device and connectivity modules, without potential to damage components of the measuring device.

However, it will be appreciated that this is not essential, and alternatively, the measuring device could be provided within the connectivity module housing, and hence not require a separate measuring device housing. In this instance, the connectivity module housing could include a door, cover, lid or other opening, that provides access to the inside of the connectivity module, and the second connector provided therein. This allows the measuring device to be inserted into the connectivity module housing and coupled to the second connector, in a manner substantially similar to that described above, albeit with the measuring device contained entirely within the connectivity module housing.

For example, the measuring device could include a circuit board, having the relevant components and first connector mounted thereon. This could be supported internally within the connectivity module, either through physical engagement between the first and second connectors, or through cooperation with a separate bracket or other mounting. Thus, it will be appreciated that this arrangement could be analogous to the manner in which a card, such as a graphics card or RAM is installed in a computer system housing through attachment to a motherboard, with the measuring device corresponding to the card, and the connectivity module the computer system and motherboard.

In this latter arrangement, it would be typically although not essential for the measuring device to be mounted in a single connectivity module, as opposed to being used interchangeably with different connectivity modules, to thereby ensure components of the measuring device are not damaged. Nevertheless, this would still allow for common measuring devices to be used with a wide range of different connectivity modules, thereby reducing manufacturing complexity and requirements, whilst still allowing a wide range of functionality to be achieved.

It will be appreciated that features from different examples above may be used interchangeably where appropriate. Furthermore, whilst the above examples have focused on a subject such as a human, it will be appreciated that the measuring device and techniques described above can be used with any animal, including but not limited to, primates, livestock, performance animals, such race horses, or the like. The above described processes can be used for diagnosing the presence, absence or degree of a range of conditions and illnesses, including, but not limited to oedema, lymphodema, body composition, or the like, and reference to specific indicators is not intended to be limiting.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The invention claimed is:

1. A system for performing at least one impedance measurement on a biological subject, the system including:

a) a measuring device including:
  i) at least one signal generator that generates a drive signal;
  ii) at least one sensor that measures a response signal;
  iii) a measuring device processor that at least in part controls the at least one signal generator and receives an indication of a measured response signal from the at least one sensor, allowing the at least one impedance measurement to be performed; and,
  iv) a first connector electrically connected to the at least one sensor and the at least one signal generator; and,
b) a connectivity module including:
  i) a connectivity module housing;
  ii) electrodes that are provided in electrical contact with the subject in use; and,
  iii) a second connector electrically connected to the electrodes, wherein in use the measuring device is connected to the connectivity module by interconnecting the first and second connectors so that first electrodes of the electrodes of the connectivity module are electrically connected to the at least one signal generator and second electrodes of the electrodes of the connectivity module are electrically connected to the at least one sensor, thereby allowing the drive signal to be applied to the subject via the first electrodes and allowing the response signal to be measured via the second electrodes so that the at least one impedance measurement can be performed, wherein the connectivity module includes:
    a first housing including spaced pairs of footplate electrodes of the electrodes of the connectivity module, each pair of footplate electrodes of the spaced pairs of footplate electrodes including a foot drive electrode and a foot sense electrode, wherein said each pair of footplate electrodes is configured to be placed in contact with a respective foot of the biological subject, the first housing maintaining the foot drive electrodes and the foot sense electrodes in respective fixed positions spaced apart from one another; and,
    a second housing including spaced pairs of handplate electrodes of the electrodes of the connectivity module, each pair of handplate electrodes of the spaced pairs of handplate electrodes including a hand drive electrode and a hand sense electrode, and wherein said each pair of handplate electrode is configured to be placed in contact with a respective hand of the biological subject, the second housing maintaining the hand drive electrodes and the hand sense electrodes in respective fixed positions spaced apart from one another;
    wherein the second housing includes a raised portion between each pair of the hand drive electrodes and the hand sense electrodes of the spaced pairs of handplate electrodes, the raised portion defining thumb recesses to thereby guide positioning of a subject's hands relative to each pair of hand drive electrodes and hand sense electrodes in use, and
    wherein the first and second housings comprise rigid material defining a first recess and a second recess, a first pair of footplate electrodes of the spaced pairs of footplate electrodes located within the first recess and a second pair of footplate electrodes of the spaced pairs of footplate electrodes located within the second recess.

2. A system according to claim 1, wherein the measuring device is adapted to be used with a number of different connectivity module types, and wherein the measuring device processor performs the at least one impedance measurement at least in part depending on a connectivity module type of a connected connectivity module and wherein the measuring device processor:
  a) determines the connectivity module type of the connected connectivity module; and,
  b) in accordance with the determined connectivity module type, at least one of:
    i) causes the at least one impedance measurement to be performed; and,
    ii) processes a measured response signal to determine at least one impedance value indicative of a measured impedance.

3. A system according to claim 2, wherein the connectivity module type is determined using at least one of:
  a) a configuration of connections between the first connector and the second connector;
  b) at least in part on connections between individual connections of the second connector when the first connector and the second connector include a plurality of individual connections;
  c) using an identifier associated with the connectivity module;
  d) using an identifier retrieved from memory of the connectivity module via at least one of:
    i) a wireless connection; and,
    ii) the first connector and the second connector;
  e) a configuration of the second connector; and,
  f) a property of an electrical component electrically connected to the second connector.

4. A system according to claim 2, wherein the measuring device includes at least one contact switch, and wherein the switch is selectively actuated by the connectivity module housing when the measuring device and the connectivity module are connected.

5. A system according to claim 1, wherein the connectivity module includes a memory and wherein the measuring device processor:
  a) retrieves instructions from the memory via at least one of:
    i) a wireless connection; and,
    ii) the first connector and the second connector; and,
  b) causes at least one impedance measurement to be performed in accordance with the instructions.

6. A system according to claim 1, wherein the measuring device processor determines at least one impedance value indicative of at least one measured impedance using:
  a) an indication of at least one drive signal applied to the subject;
  b) an indication of at least one measured response signal; and,
  c) calibration data stored in a memory.

7. A system according to claim 6, wherein at least one of:
  a) the calibration data includes:
    i) first calibration data specific to the measuring device; and,
    ii) second calibration data specific to the connectivity module;
  b) the calibration data is determined at least in part using at least one of:
    i) a connectivity module type; and,
    ii) a connectivity module identifier; and,
    iii) the measuring device processor selects one of a number of calibration data sets stored in the memory.

8. A system according to claim 1, wherein the measuring device housing and connectivity module housing are configured to physically interconnect when the measuring device is connected to the connectivity module.

9. A system according to claim 1, wherein the electrodes are at least one of:
   a) mounted on the connectivity module housing; and,
   b) coupled to leads extending from the connectivity module housing.

10. A system according to claim 1, wherein the measuring device includes a switching unit for selectively electrically connecting the at least one signal generator and the at least one sensor to the first connector thereby allowing the at least one signal generator and the at least one sensor to be selectively connected to different electrodes of the connectivity module and wherein the measuring device processor controls the switching unit to thereby selectively electrically connect the at least one signal generator and the at least one sensor to respective electrodes of the connectivity module thereby allowing a respective impedance measurement to be performed.

11. A system according to claim 1, wherein the measuring device includes:
   a) four signal generators, each being electrically connected to a respective drive electrode of the electrodes of the connectivity module; and,
   b) four sensors, each being electrically connected to a respective sense electrode of the electrodes of the connectivity module and wherein the measuring device processor selectively activates the four signal generators and the four sensors to thereby allow a respective impedance measurement to be performed.

12. A system according to claim 1, wherein the measuring device includes at least one of:
   a) an input button that at least one of:
      i) activates the measuring device; and,
      ii) causes at least one impedance measurement to be performed; and,
   b) an indicator, and wherein the measuring device processor uses the indicator to indicate at least one of:
      i) completion of an impedance measurement;
      ii) performing of an impedance measurement;
      iii) connection of the measuring device to at least one of:
         (1) the connectivity module; and,
         (2) a processing system; and,
      wherein the indicator includes at least one of:
      i) an optical indicator;
      ii) a multi-colour LED; and,
      iii) a speaker.

13. A system according to claim 1, wherein the measuring device includes an interface that allows the measuring device processor to communicate with a processing system using at least one of wired and wireless communications, and wherein:
   b) the processing system:
      i) determines the at least one impedance measurement to be performed;
      ii) causes the measuring device to perform the at least one impedance measurement; and,
      iii) receives an indication of at least one impedance value from the measuring device, the at least one impedance value being indicative of a measured impedance; and,
   c) the measuring device processor communicates with the processing system to at least one of:
      i) determine the at least one impedance measurement to be performed; and,
      ii) provide the indication of the at least one impedance value to the processing system.

14. A system according to claim 13, wherein the processing system:
   d) determines an impedance measurement process to be performed, the impedance measurement process including a sequence of impedance measurements; and,
   e) causes the measuring device processor to perform the sequence of impedance measurements.

15. A system according to claim 13, wherein the processing system at least one of:
   a) processes the at least one impedance measurement to determine at least one indicator indicative of a biological state of the subject; and,
   b) displays a user interface allowing a user to at least one of:
      i) select at least one impedance measurement to be performed;
      ii) select an impedance measurement process to be performed, the impedance measurement process including a sequence of impedance measurements;
      iii) view at least one impedance measurement of the impedance measurements; and,
      iv) view at least one indicator indicative of a biological state of the subject.

16. A system according to claim 13, wherein:
   a) the measuring device processor:
      i) determines at least one performable impedance measurement based on a connectivity module type of a connected connectivity module;
      ii) provides an indication of the at least one performable impedance measurement to the processing system; and,
   b) the processing system:
      i) displays an indication of the at least one performable impedance measurement to a user;
      ii) determines a selected performable impedance measurement in accordance with user input commands; and,
      iii) causes the measuring device to perform the selected performable impedance measurement.

17. A system according to claim 1, wherein the system includes a processing system that:
   a) determines at least one performable impedance measurement based on a connectivity module type of a connectivity module connected to the measuring device;
   b) displays an indication of the at least one performable impedance measurement to a user;
   c) determines a selected performable impedance measurement in accordance with user input commands;
   d) causes the measuring device to perform the selected performable impedance measurement; and,
   e) determines at least one impedance value indicative of a measured impedance.

18. A system according to claim 1, wherein the first housing includes a raised lip extending at least partially around each pair of foot drive and sense electrodes to thereby guide positioning of a subject's foot relative to the foot drive and sense electrodes in use and wherein the raised lip is configured to engage at least a heel of the biological subject.

19. A system according to claim 1, wherein the second housing at least one of:
   a) is shaped to at least partially conform to a shape of the hands of the biological subject; and, b) includes a processing system mounting that in use receives a support containing a processing system.

20. A system according to claim 1, wherein at least one of the first and second housings include keyhole mountings, allowing the at least one of the first housing and the second housing to be removably mounted to a pedestal.

21. A system according to claim 1, wherein the first housing and the second housing comprise rigid structures, wherein the first housing comprises a first dividing portion extending between the first spaced pair of footplate electrodes and the second spaced pair of footplate electrodes to space the first spaced pair of footplate electrodes and the second pairs of footplate electrodes apart from each other, and wherein the second housing comprises a second dividing portion extending between the first spaced pair of handplate electrodes and the second spaced pair of handplate electrodes to space the first spaced pair of hand plate electrodes and the second spaced pair of handplate electrodes apart from each other.

22. A system according to claim 1, wherein the first housing and the second housing comprise rigid, non-conductive material spacing the first spaced pairs of footplate electrodes and the second spaced pair of footplate electrodes apart from one another, and spacing the first spaced pair of handplate electrodes and the second spaced pair of handplate electrodes apart from one another.

* * * * *